(12) United States Patent
John Archibald

(10) Patent No.: US 12,667,261 B2
(45) Date of Patent: Jun. 30, 2026

(54) SELECTIVE PHOTOACOUSTIC SAMPLING FOR BLOOD PRESSURE PREDICTION

(71) Applicant: QUALCOMM Incorporated, San Diego, CA (US)

(72) Inventor: Fitzgerald John Archibald, Richmond Hill (CA)

(73) Assignee: QUALCOMM Incorporated, San Diego, CA (US)

( * ) Notice: Subject to any disclaimer, the term of this patent is extended or adjusted under 35 U.S.C. 154(b) by 70 days.

(21) Appl. No.: 18/461,026

(22) Filed: Sep. 5, 2023

(65) Prior Publication Data

US 2025/0072759 A1     Mar. 6, 2025

(51) Int. Cl.
| | |
|---|---|
| *A61B 5/00* | (2006.01) |
| *A61B 5/021* | (2006.01) |
| *A61B 5/024* | (2006.01) |

(52) U.S. Cl.
CPC ............ *A61B 5/0095* (2013.01); *A61B 5/021* (2013.01); *A61B 5/02444* (2013.01); *A61B 5/742* (2013.01)

(58) Field of Classification Search
CPC ... A61B 5/0095; A61B 5/021; A61B 5/02444; A61B 5/742
See application file for complete search history.

(56) References Cited

U.S. PATENT DOCUMENTS

| | | | | |
|---|---|---|---|---|
| 7,515,948 B1 * | 4/2009 | Balberg | ............... | A61B 5/1464 |
| | | | | 600/338 |
| 9,554,738 B1 * | 1/2017 | Gulati | ................... | A61B 5/0075 |
| 2011/0098550 A1 * | 4/2011 | Yoda | .................... | A61B 5/0059 |
| | | | | 600/407 |

(Continued)

FOREIGN PATENT DOCUMENTS

| | | | | |
|---|---|---|---|---|
| WO | WO-2019031607 A1 * | 2/2019 | ............. | A61B 8/543 |
| WO | WO-2021183406 A1 * | 9/2021 | ......... | A61B 5/02007 |

OTHER PUBLICATIONS

Gao, X., Chen, X., Hu, H. et al. A photoacoustic patch for three-dimensional imaging of hemoglobin and core temperature. Nat Commun 13, 7757 (2022). https://doi.org/10.1038/s41467-022-35455-3 (Year: 2022).*

(Continued)

*Primary Examiner* — Joel Lamprecht
*Assistant Examiner* — James F McDonald, III
(74) *Attorney, Agent, or Firm* — Weaver Austin Villeneuve & Sampson LLP

(57)     ABSTRACT

Some disclosed methods involve monitoring a heart rate waveform associated with a subject to detect cardiac cycle markers, determining a cardiac phase transition window based on the cardiac cycle markers, and activating a photoacoustic sampling system at a start of the cardiac phase transition window, the photoacoustic sampling system including a piezoelectric receiver and a light source system. Such methods may involve, during the cardiac phase transition window, controlling the light source system to emit a plurality of light pulses into biological tissue of the subject, receiving, from the piezoelectric receiver, signals corresponding to acoustic waves emitted from portions of the biological tissue, and obtaining plethysmography data based on the signals. Such methods may involve deactivating the photoacoustic sampling system by an end of the cardiac phase transition window.

24 Claims, 16 Drawing Sheets

450

(56) References Cited

U.S. PATENT DOCUMENTS

| | | | |
|---|---|---|---|
| 2012/0083703 A1 | 4/2012 | Blomqvist et al. | |
| 2013/0190589 A1* | 7/2013 | Chen | A61B 5/145 |
| | | | 600/407 |
| 2013/0190596 A1* | 7/2013 | Oraevsky | A61B 5/004 |
| | | | 600/407 |
| 2014/0024916 A1* | 1/2014 | Hautvast | A61B 5/7289 |
| | | | 600/407 |
| 2014/0114147 A1* | 4/2014 | Romesburg | A61B 5/725 |
| | | | 600/301 |
| 2016/0150991 A1* | 6/2016 | Ohkoba | A61B 5/352 |
| | | | 600/407 |
| 2016/0220129 A1 | 8/2016 | Ostroverkhov et al. | |
| 2016/0361041 A1* | 12/2016 | Barsimantov | A61B 8/065 |
| 2017/0095211 A1* | 4/2017 | Wang | A61B 5/721 |
| 2017/0323132 A1* | 11/2017 | Lu | A61B 5/0095 |
| 2019/0220642 A1* | 7/2019 | Lu | G06V 40/1382 |
| 2019/0269334 A1* | 9/2019 | Addison | G06F 17/11 |
| 2020/0229789 A1* | 7/2020 | Yamamoto | A61B 8/4281 |
| 2021/0030280 A1* | 2/2021 | Oraevsky | A61B 5/026 |
| 2021/0275086 A1 | 9/2021 | Van Berkel | |
| 2022/0175258 A1* | 6/2022 | Kitchens | A61B 5/02116 |
| 2023/0293035 A1* | 9/2023 | Heym | A61B 5/02108 |
| | | | 600/481 |

OTHER PUBLICATIONS

International Search Report and Written Opinion—PCT/US2024/045161—ISA/EPO—Nov. 15, 2024.

* cited by examiner

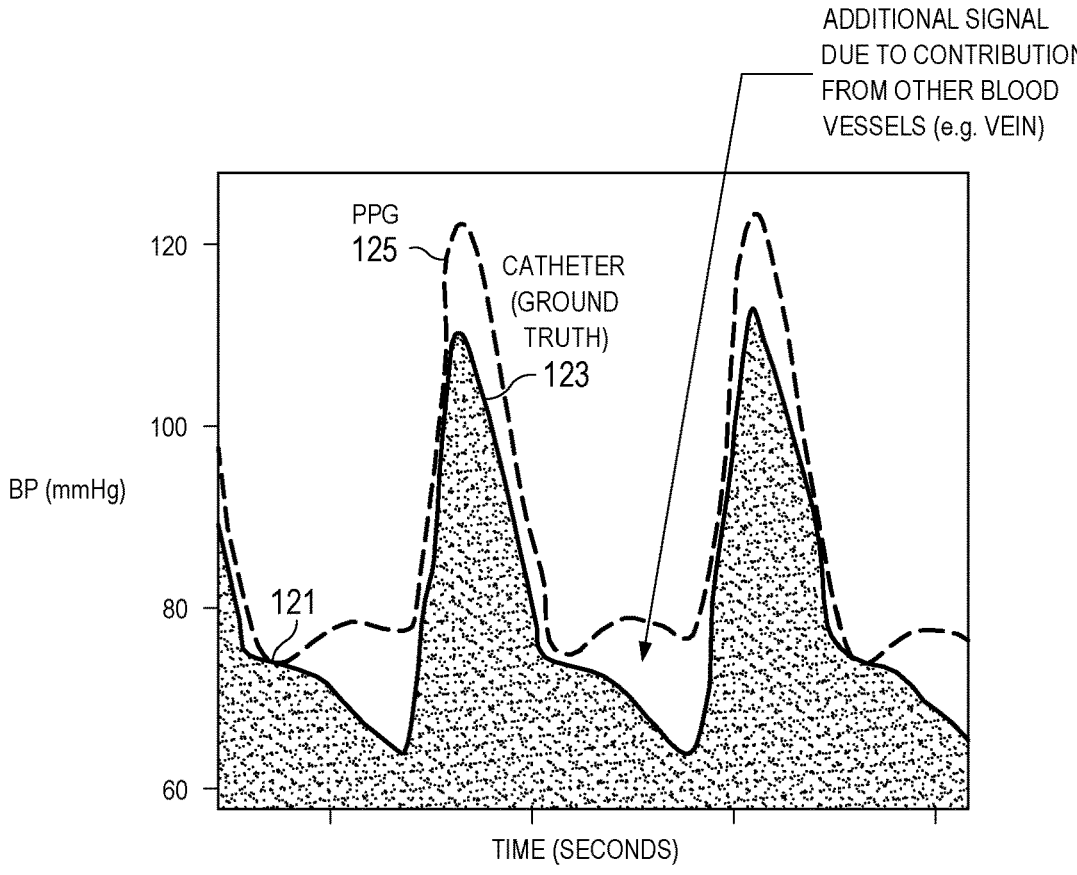
ADDITIONAL SIGNAL
DUE TO CONTRIBUTION
FROM OTHER BLOOD
VESSELS (e.g. VEIN)
*Figure 1B*
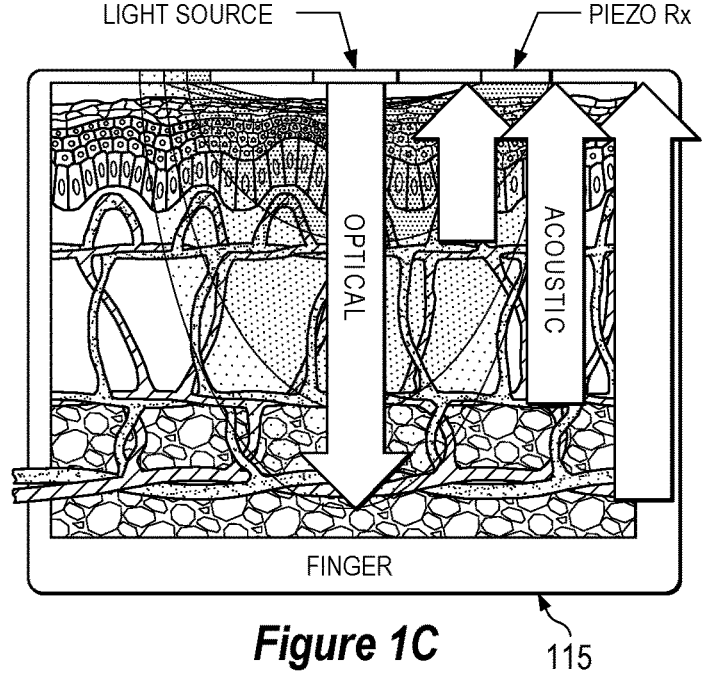
*Figure 1C*          115

300

350

400

600

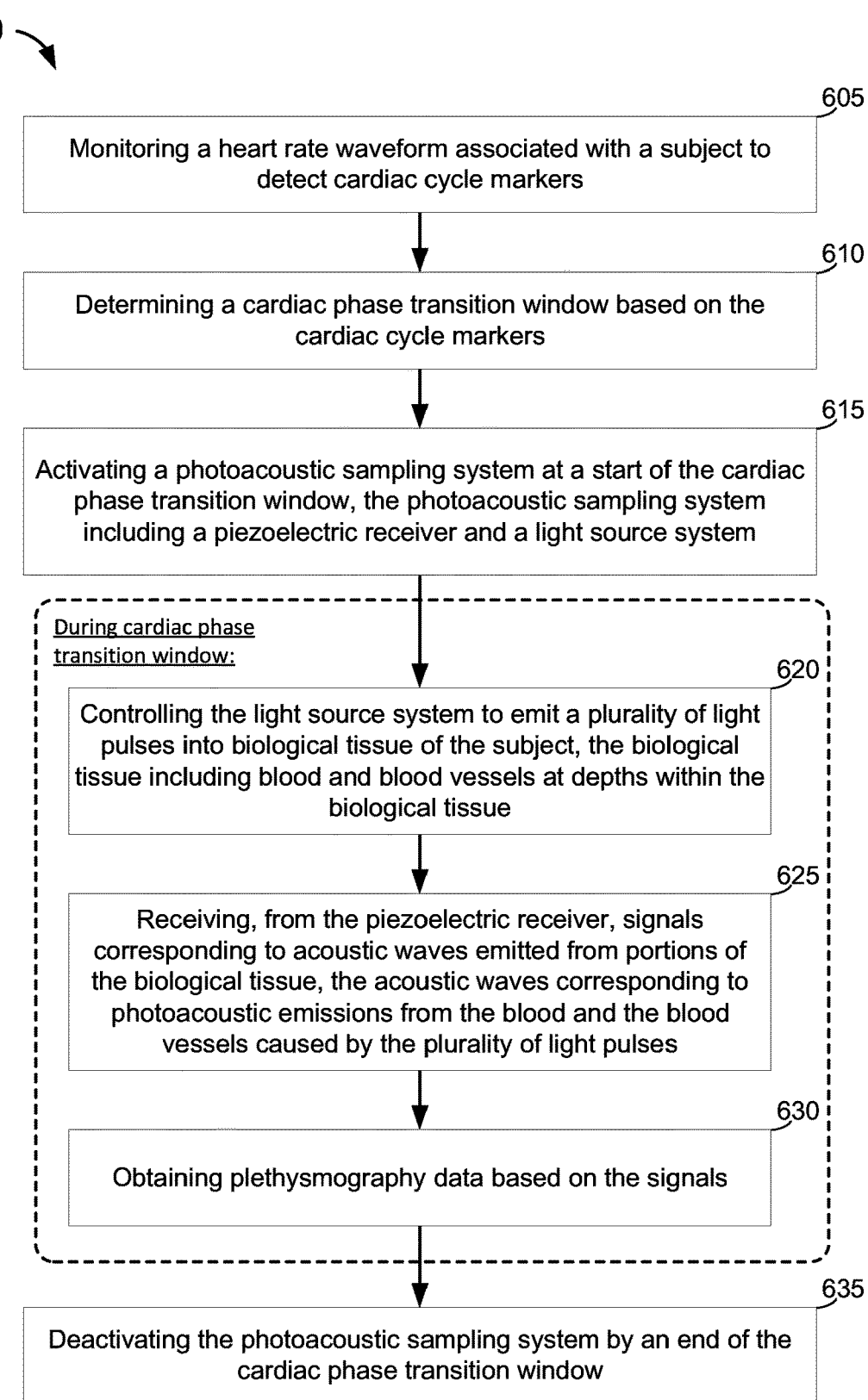

605

Monitoring a heart rate waveform associated with a subject to detect cardiac cycle markers

610

Determining a cardiac phase transition window based on the cardiac cycle markers

615

Activating a photoacoustic sampling system at a start of the cardiac phase transition window, the photoacoustic sampling system including a piezoelectric receiver and a light source system During cardiac phase transition window:

620

Controlling the light source system to emit a plurality of light pulses into biological tissue of the subject, the biological tissue including blood and blood vessels at depths within the biological tissue

625

Receiving, from the piezoelectric receiver, signals corresponding to acoustic waves emitted from portions of the biological tissue, the acoustic waves corresponding to photoacoustic emissions from the blood and the blood vessels caused by the plurality of light pulses

630

Obtaining plethysmography data based on the signals

635

Deactivating the photoacoustic sampling system by an end of the cardiac phase transition window

SELECTIVE PHOTOACOUSTIC SAMPLING FOR BLOOD PRESSURE PREDICTION

TECHNICAL FIELD

This disclosure relates generally to non-invasive blood pressure estimation and blood vessel monitoring.

DESCRIPTION OF RELATED TECHNOLOGY

A variety of different sensing technologies and algorithms are being investigated for use in various biomedical applications, including health and wellness monitoring. This push is partly a result of the limitations in the usability of traditional measuring devices for continuous, noninvasive and ambulatory monitoring. For example, a sphygmomanometer is an example of a traditional blood pressure monitoring device that utilizes an inflatable cuff to apply a counter pressure to a region of interest (for example, around an upper arm of a subject). The pressure exerted by the inflatable cuff is designed to restrict arterial flow in order to provide a measurement of systolic and diastolic pressure. Such traditional sphygmomanometers inherently affect the physiological state of the subject, which can introduce an error in the blood pressure measurements. Such sphygmomanometers also can affect the psychological state of the subject, which can manifest itself in a physiological state change, and thus, introduce an error in the blood pressure measurements. For example, such devices are often used primarily on isolated occasions, for example, when a subject visits a doctor's office or is being treated in a hospital setting. Naturally, some subjects experience anxiety during such occasions, and this anxiety can influence (for example, increase) the user's blood pressure as well as heart rate.

For these and other reasons, such devices may not provide an accurate estimation or "picture" of blood pressure, and a user's health in general, over time. While implanted or otherwise invasive devices may provide better estimates of blood pressure over time, such invasive devices generally involve greater risk than noninvasive devices and are generally not suitable for ambulatory use.

SUMMARY

The systems, methods and devices of this disclosure each have several aspects, no single one of which is solely responsible for the desirable attributes disclosed herein.

One innovative aspect of the subject matter described in this disclosure can be implemented in an apparatus, or in a system that includes the apparatus. The apparatus may include a heart rate waveform analyzer, a photoacoustic sampling system, and a control system. The photoacoustic sampling system may include an ultrasonic receiver (e.g., a piezoelectric receiver) and a light source system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

The heart rate waveform analyzer may be configured for monitoring a heart rate waveform associated with a subject to detect cardiac cycle markers, and determining a cardiac phase transition window based on the cardiac cycle markers. The control system may be configured for activating the photoacoustic sampling system at a start of the cardiac phase transition window, and during the cardiac phase transition window, controlling the light source system to emit a plurality of light pulses into biological tissue of the subject, receiving, from the piezoelectric receiver, signals corresponding to acoustic waves emitted from portions of the biological tissue, and obtaining plethysmography data based on the signals. The biological tissue may, for example, include blood and blood vessels at depths within the biological tissue. The acoustic waves may, for example, correspond to photoacoustic emissions from the blood and the blood vessels caused by the plurality of light pulses. The control system may be configured for deactivating the photoacoustic sampling system by an end of the cardiac phase transition window.

According to some implementations, the control system may be further configured to deactivate the photoacoustic sampling system prior to the end of the cardiac phase transition window responsive to a determination, prior to the end of the cardiac phase transition window, that the plethysmography data includes at least a threshold number of samples. According to some implementations, the cardiac phase transition window may correspond to a systolic-to-diastolic transition. According to some other implementations, the cardiac phase transition window may correspond to a diastolic-to-systolic transition.

According to some implementations, the heart rate waveform analyzer may be further configured to obtain the heart rate waveform based on a data stream received from a heart activity sensor. According to some implementations, the control system may be further configured to determine a blood pressure based on the plethysmography data and display the blood pressure on a display. According to some implementations, the control system may be further configured to determine the blood pressure based on systolic phase data comprised in the plethysmography data, without reference to diastolic phase data comprised in the plethysmography data.

According to some implementations, the plethysmography data may be photoacoustic plethysmography (PAPG) data. According to some implementations, the control system may be further configured to generate a two-dimensional (2D) PAPG image based on the PAPG data. According to some implementations, the 2D PAPG image may comprise a depth time dimension and a pulse time dimension.

Other innovative aspects of the subject matter described in this disclosure can be implemented in a method, such as a biometric method. The method may involve monitoring a heart rate waveform associated with a subject to detect cardiac cycle markers, determining a cardiac phase transition window based on the cardiac cycle markers, and activating a photoacoustic sampling system at a start of the cardiac phase transition window. The photoacoustic sampling system may include an ultrasonic receiver (e.g., a piezoelectric receiver) and a light source system. The method may involve, during the cardiac phase transition window, controlling the light source system to emit a plurality of light pulses into biological tissue of the subject, receiving, from the piezoelectric receiver, signals corresponding to acoustic waves emitted from portions of the biological tissue, and obtaining plethysmography data based on the signals. The biological tissue may, for example, include blood and blood vessels at depths within the biological tissue. The acoustic waves may, for example, correspond to photoacoustic emissions from the blood and the blood vessels caused by the plurality of light pulses. The method may involve deactivating the photoacoustic sampling system by an end of the cardiac phase transition window.

According to some implementations, the method may further involve deactivating the photoacoustic sampling system prior to the end of the cardiac phase transition window responsive to a determination, prior to the end of the cardiac phase transition window, that the plethysmography data includes at least a threshold number of samples. According to some implementations, the cardiac phase transition window may correspond to a systolic-to-diastolic transition. According to some other implementations, the cardiac phase transition window may correspond to a diastolic-to-systolic transition.

According to some implementations, the method may further involve obtaining the heart rate waveform based on a data stream received from a heart activity sensor. According to some implementations, the method may further involve determining a blood pressure based on the plethysmography data and displaying the blood pressure on a display. According to some implementations, the method may further involve determining the blood pressure based on systolic phase data comprised in the plethysmography data, without reference to diastolic phase data comprised in the plethysmography data.

According to some implementations, the plethysmography data may be photoacoustic plethysmography (PAPG) data. According to some implementations, the method may further involve generating a two-dimensional (2D) PAPG image based on the PAPG data. According to some implementations, the 2D PAPG image may comprise a depth time dimension and a pulse time dimension.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in one or more non-transitory media having software stored thereon. The software may include instructions for controlling one or more devices to perform one or more disclosed methods.

One such method may involve monitoring a heart rate waveform associated with a subject to detect cardiac cycle markers, determining a cardiac phase transition window based on the cardiac cycle markers, and activating a photoacoustic sampling system at a start of the cardiac phase transition window. The photoacoustic sampling system may include an ultrasonic receiver (e.g., a piezoelectric receiver) and a light source system. The method may involve, during the cardiac phase transition window, controlling the light source system to emit a plurality of light pulses into biological tissue of the subject, receiving, from the piezoelectric receiver, signals corresponding to acoustic waves emitted from portions of the biological tissue, and obtaining plethysmography data based on the signals. The biological tissue may, for example, include blood and blood vessels at depths within the biological tissue. The acoustic waves may, for example, correspond to photoacoustic emissions from the blood and the blood vessels caused by the plurality of light pulses. The method may involve deactivating the photoacoustic sampling system by an end of the cardiac phase transition window.

According to some implementations, the method may further involve deactivating the photoacoustic sampling system prior to the end of the cardiac phase transition window responsive to a determination, prior to the end of the cardiac phase transition window, that the plethysmography data includes at least a threshold number of samples. According to some implementations, the cardiac phase transition window may correspond to a systolic-to-diastolic transition. According to some other implementations, the cardiac phase transition window may correspond to a diastolic-to-systolic transition.

According to some implementations, the method may further involve obtaining the heart rate waveform based on a data stream received from a heart activity sensor. According to some implementations, the method may further involve determining a blood pressure based on the plethysmography data and displaying the blood pressure on a display. According to some implementations, the method may further involve determining the blood pressure based on systolic phase data comprised in the plethysmography data, without reference to diastolic phase data comprised in the plethysmography data.

According to some implementations, the plethysmography data may be photoacoustic plethysmography (PAPG) data. According to some implementations, the method may further involve generating a two-dimensional (2D) PAPG image based on the PAPG data. According to some implementations, the 2D PAPG image may comprise a depth time dimension and a pulse time dimension.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 1B shows an example of two superimposed graphs of blood pressure variation during cardiac cycles.

FIG. 1C shows an example of a blood pressure monitoring device based on photoacoustic plethysmography, which may be referred to herein as PAPG.

FIG. 6 illustrates an example method according to aspects of the disclosure.

Like reference numbers and designations in the various drawings indicate like elements.

DETAILED DESCRIPTION

Figure 1A:
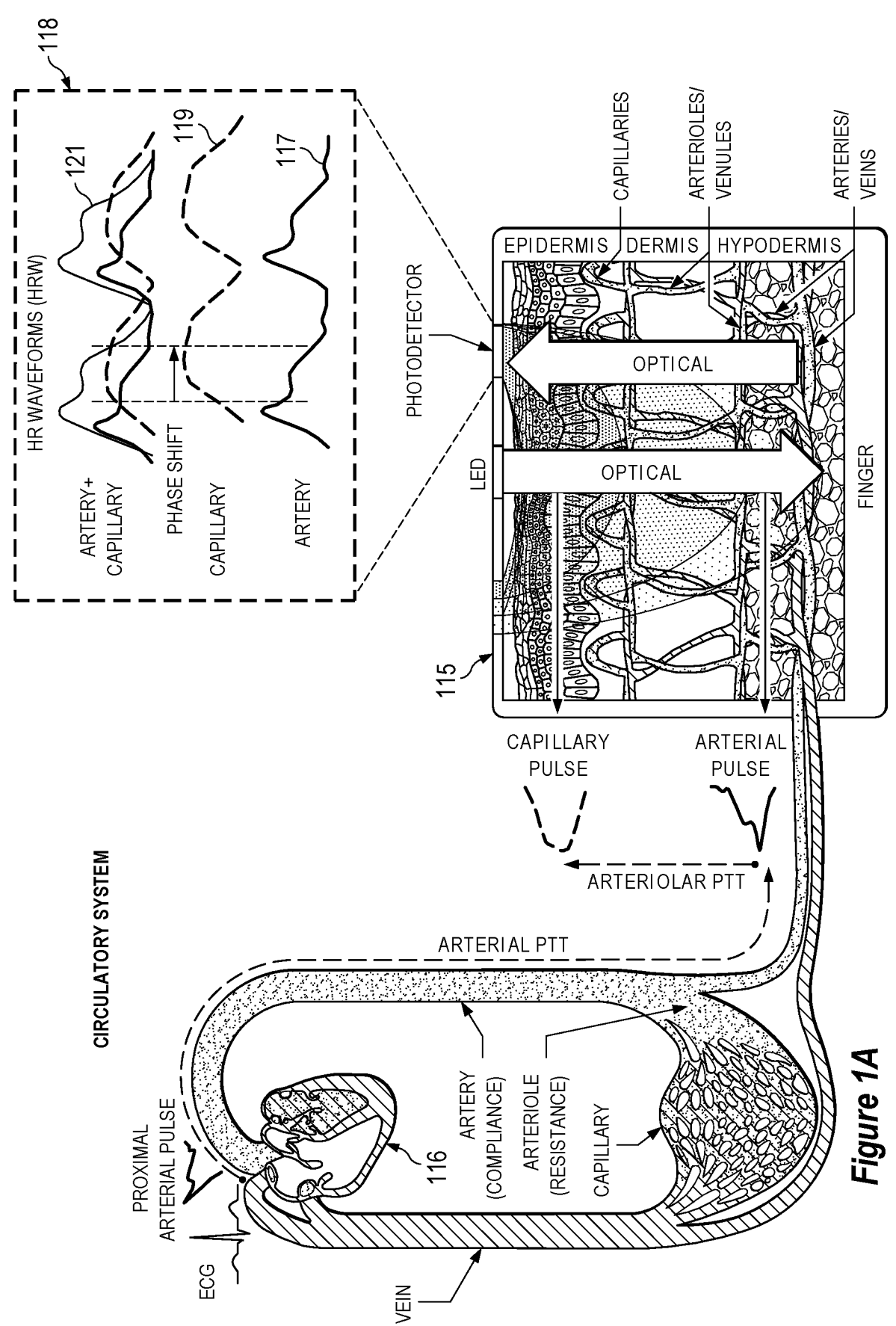
FIG. 1A shows an example of a blood pressure monitoring device based on photoplethysmography (PPG).

The following description is directed to certain implementations for the purposes of describing various aspects of this disclosure. However, a person having ordinary skill in the art will readily recognize that the teachings herein can be applied in a multitude of different ways. Some of the concepts and examples provided in this disclosure are especially applicable to blood pressure monitoring applications. However, some implementations also may be applicable to other types of biological sensing applications, as well as to other fluid flow systems. The described implementations may be implemented in any device, apparatus, or system that includes an apparatus as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), architectural structures, microwaves, refrigerators, stereo systems, cassette recorders or players, DVD players, CD players, VCRs, radios, portable memory chips, washers, dryers, washer/dryers, parking meters, automobile doors, autonomous or semi-autonomous vehicles, drones, Internet of Things (IoT) devices, etc. Thus, the teachings are not intended to be limited to the specific implementations depicted and described with reference to the drawings; rather, the teachings have wide applicability as will be readily apparent to persons having ordinary skill in the art.

Also of note, the conjunction "or" as used herein is intended in the inclusive sense where appropriate unless otherwise indicated; that is, the phrase "A, B or C" is intended to include the possibilities of A individually; B individually; C individually; A and B and not C; B and C and not A; A and C and not B; and A and B and C. Similarly, a phrase referring to "at least one of" a list of items refers to any combination of those items, including single members. As an example, the phrase "at least one of A, B, or C" is intended to cover the possibilities of at least one of A; at least one of B; at least one of C; at least one of A and at least one of B; at least one of B and at least one of C; at least one of A and at least one of C; and at least one of A, at least one of B and at least one of C.

Various aspects relate generally to blood pressure monitoring, and more particularly to non-invasive blood pressure monitoring using plethysmography. Some aspects more specifically relate to blood pressure prediction using two-dimensional (2D) photoacoustic plethysmography (PAPG). In various implementations, blood pressures of a subject can be predicted based on 2D PAPG image segments. The 2D PAPG image segments can be obtained using a segment generation process that includes performing photoacoustic sampling to obtain raw 2D PAPG data, constructing 2D PAPG images based on the raw 2D PAPG data, and segmenting the 2D PAPG images on a per-heart rate cycle basis. According to aspects of the disclosure, the photoacoustic sampling and 2D PAPG image construction can be performed selectively, so as to obtain 2D PAPG imagery corresponding to portions of the subject's heart rate cycle that are of significance with respect to 2D PAPG-based blood pressure prediction while refraining from raw 2D PAPG data capture and processing with respect to portions of the heart rate cycle that are not of significance. According to aspects of the disclosure, the significant portions of the heart rate cycle can correspond to cardiac phase transition windows representing time intervals during which cardiac phase transitions—such as systolic-to-diastolic transitions, diastolic-to-systolic transitions, or both—occur. According to various implementations, blood pressures can be predicted based on the 2D PAPG image segments using a prediction model trained using a deep learning network (DLN), such as a long short-term memory (LSTM) neural network or a convolutional neural network (CNN).

According to aspects of the disclosure, rather than being identified via 2D PAPG-based analysis, such cardiac phase transition windows can be identified via a non-PAPG-based procedure operating in parallel. For instance, according to various implementations, a PPG-based phase transition detection process may be implemented, according to which a photoplethysmography (PPG) device may be used to obtain heart rate waveforms associated with the subject, and the heart rate waveforms may be analyzed to determine cardiac phase transition windows associated with the subject.

Particular implementations of the subject matter described in this disclosure can be implemented to realize one or more of the following potential advantages. According to some implementations, the use of a deep learning network-trained model to estimate differential blood pressure based on plethysmography images obtained from raw 2D PAPG data can yield more accurate differential blood pressure estimates. Performing the photoacoustic sampling and 2D PAPG image construction selectively, and thus refraining from raw 2D PAPG data capture and processing with respect to portions of the heart rate cycle that are not of significance, can enable the benefits of 2D PAPG-based blood pressure prediction to be realized at reduced cost with respect to power consumption and processing and memory resource utilization.

Some implementations of the portable monitoring devices described herein also are designed to consume relatively little power, enabling continuous wearing and monitoring of a biological signal of interest, such as blood pressure, over extended durations of time (for example, hours, days, weeks or even a month or more) without external calibration, recharging or other interruption. Continuous monitoring provides greater prognostic and diagnostic value than isolated measurements, for example, obtained in a hospital or doctor's office setting. Some implementations of the portable or "ambulatory" monitoring devices described herein also are designed with small form factors and with housings that can be coupled to a subject (also referred to herein as a "patient," "person" or "user") so as to be wearable, noninvasive, and nonrestrictive of ambulatory use. In other words, some implementations of the ambulatory monitoring devices described herein do not restrict the free uninhibited motion of a subject's arms or legs enabling continuous or periodic monitoring of cardiovascular characteristics such as blood pressure even as the subject is mobile or otherwise engaged in a physical activity. Not only do such devices not interfere with the subject's daily or other desired activities, they also may encourage continuous wearing by virtue of such non-interference. In some implementations, it can further be desirable that the subject may have no notion about when the sensing device(s) of the ambulatory monitoring device is actually performing measurements.

Moreover, some disclosed implementations provide advantages compared to previously-deployed non-invasive blood pressure monitoring devices, such as those based on photoplethysmography (PPG). PPG-based blood pressure monitoring devices are not optimal because PPG superimposes data corresponding to the blood volume of all illuminated blood vessels (arteries, veins, etc.), each of which exhibit unique blood volume changes over time, thereby producing a blended signal that is not closely correlated to blood pressure and is susceptible to drift. In contrast, some disclosed devices apply depth-discriminated photoacoustic plethysmography (PAPG) methods, which can distinguish artery heart rate waveforms from vein heart rate waveforms and other heart rate waveforms. Blood pressure estimation based on depth-discriminated PAPG methods can be substantially more accurate than blood pressure estimation based on PPG-based methods.

Continuous blood pressure monitoring can be important component of patient care with respect to a wide variety of medical conditions. According to some approaches, continuous blood pressure monitoring can be established using an implanted, or otherwise invasive device, such as a catheter. However, an invasive blood pressure monitoring device can negatively impact patient comfort, can create a risk of infection, and can be unsuitable for ambulatory use. In many cases, it may be desirable to conduct continuous, non-invasive and ambulatory monitoring of a patient's blood pressure monitoring.

Some non-invasive blood pressure monitoring devices can monitor blood pressure using plethysmography. In the general sense, plethysmography involves measuring changes in the volume of an organ, a part of the body, or the body as a whole. Blood pressure monitoring using plethysmography generally involves estimating blood pressure based on measurements of volumetric changes in the blood in a part of the body.

Photoplethysmography (PPG) is one type of plethysmography that can be used for blood pressure monitoring. PPG involves transmitting light onto an area of human tissue, such as tissue of a finger, measuring light reflected from the tissue, and analyzing the reflected light measurements to detect volumetric changes in the blood of the illuminated area.

FIG. 1A shows an example of a blood pressure monitoring device based on PPG. FIG. 1A shows examples of arteries, veins, arterioles, venules and capillaries of a circulatory system, including those inside a finger 115. In the example shown in FIG. 1A, an electrocardiogram sensor has detected a proximal arterial pulse near the heart 116.

According to the example shown in FIG. 1A, a light source that includes one or more light-emitting diodes (LEDs) has transmitted light (in some examples, green, red, and/or near-infrared (NIR) light) that has penetrated the tissues of the finger 115 in an illuminated zone. Reflections from these tissues, detected by the photodetector, may be used to detect volumetric changes in the blood of the illuminated zone of the finger 115 that correspond to heart rate waveforms.

As shown in the heart rate waveform graphs 118 of FIG. 1A, the capillary heart rate waveform 119 is differently-shaped and phase-shifted relative to the artery heart rate waveform 117. In this simple example, the detected heart rate waveform 121 is a combination of the capillary heart rate waveform 119 and the artery heart rate waveform 117. In some instances, the responses of one or more other blood vessels may also be part of the heart rate waveform 121 detected by a PPG-based blood pressure monitoring device.

FIG. 1B shows an example of two superimposed graphs of blood pressure variation during cardiac cycles. The graph 123 corresponds to blood pressure measured by a catheter, which is a sufficiently reliable method to be considered a "ground truth" against which blood pressure estimation methods can be compared. In this example, the graph 125 corresponds to blood pressure estimated by a PPG-based method. In the example shown in FIG. 1B, the areas between the graph 123 and the graph 125 indicate the errors in blood pressure estimation according to the PPG-based method.

By comparing the heart rate waveform graphs 118 of FIG. 1A and the blood pressure graphs of FIG. 1B, one can appreciate that PPG-based blood pressure monitoring devices are not optimal because PPG superimposes data corresponding to the blood volume of all illuminated blood vessels, each of which exhibit different and time-shifted blood volume changes.

An alternative type of plethysmography that may be used to monitor blood pressure more accurately is photoacoustic plethysmography (PAPG). Like PPG, PAPG involves transmitting light onto an area of human tissue, such as tissue of a finger. However, PAPG involves measuring acoustic waves (as opposed to light) reflected from the tissue, and analyzing the reflected acoustic wave measurements to detect volumetric changes in the blood of the illuminated area.

FIG. 1C shows an example of a blood pressure monitoring device based on PAPG. FIG. 1C shows the same examples of arteries, veins, arterioles, venules and capillaries inside the finger 115 that are shown in FIG. 1B. In some examples, the light source shown in FIG. 1C may be, or may include, one or more LEDs or laser diodes. In this example, as in FIG. 1A, the light source has transmitted light (in some examples, green, red, and/or near-infrared (NIR) light) that has penetrated the tissues of the finger 115 in an illuminated zone.

In the example shown in FIG. 1C, blood vessels (and components of the blood itself) are heated by the incident light from the light source and are emitting acoustic waves. In this example, the emitted acoustic waves include ultrasonic waves. According to this implementation, the acoustic wave emissions are being detected by an ultrasonic receiver, which is a piezoelectric receiver in this example. Photoacoustic emissions from the illuminated tissues, detected by the piezoelectric receiver, may be used to detect volumetric changes in the blood of the illuminated zone of the finger 115 that correspond to heart rate waveforms. In some examples, the ultrasonic receiver may correspond to the ultrasonic receiver 202 that is described below with reference to FIG. 2.

One important difference between the PPG-based system of FIG. 1A and the PAPG-based method of FIG. 1C is that the acoustic waves shown in FIG. 1C travel much more slowly than the reflected light waves shown in FIG. 1A. Accordingly, depth discrimination based on the arrival times of the acoustic waves shown in FIG. 1C is possible, whereas depth discrimination based on the arrival times of the light waves shown in FIG. 1A may not be possible. This depth discrimination allows some disclosed implementations to isolate acoustic waves received from the different blood vessels.

According to some such examples, such depth discrimination allows artery heart rate waveforms to be distinguished from vein heart rate waveforms and other heart rate waveforms. Therefore, blood pressure estimation based on depth-discriminated PAPG methods can be substantially more accurate than blood pressure estimation based on PPG-based methods.

Figure 2:
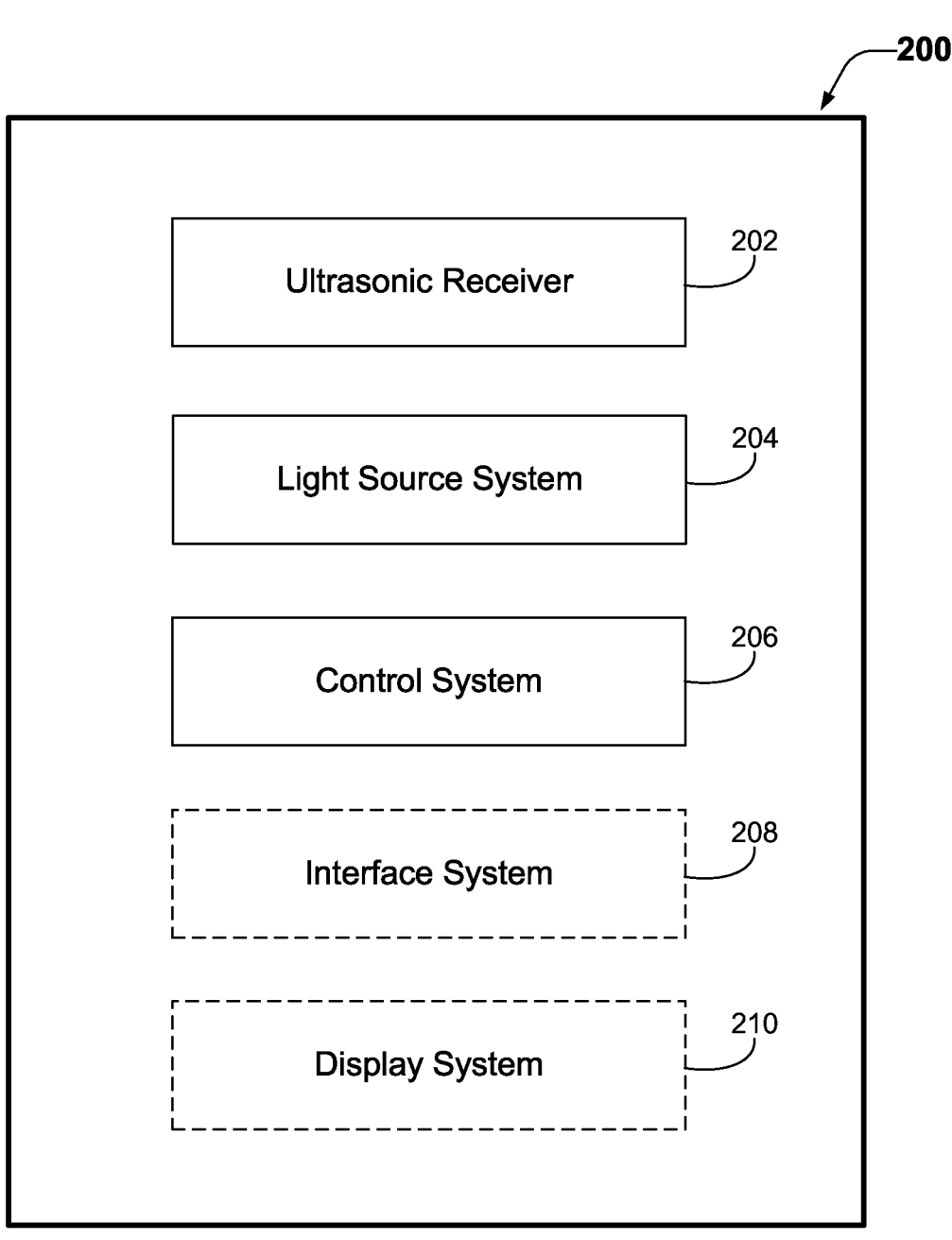
FIG. 2 is a block diagram that shows example components of an apparatus according to some examples.

FIG. 2 is a block diagram that shows example components of an apparatus according to some disclosed implementations. In this example, the apparatus 200 includes a biometric system. Here, the biometric system includes an ultrasonic receiver 202, a light source system 204 and a control system 206. Although not shown in FIG. 2, the apparatus 200 may include a substrate. In some examples, the apparatus 200 may include a platen. Some examples are described below. Some implementations of the apparatus 200 may include the interface system 208 and/or the display system 210.

Various examples of ultrasonic receivers 202 are disclosed herein, some of which may include, or be configured (or configurable) as, an ultrasonic transmitter and some of which may not. In some implementations the ultrasonic receiver 202 and an ultrasonic transmitter may be combined in an ultrasonic transceiver. In some examples, the ultrasonic receiver 202 may include a piezoelectric receiver layer, such as a layer of PVDF polymer or a layer of PVDF-TrFE copolymer. In some implementations, a single piezoelectric layer may serve as an ultrasonic receiver. In some implementations, other piezoelectric materials may be used in the piezoelectric layer, such as aluminum nitride (AlN) or lead zirconate titanate (PZT). The ultrasonic receiver 202 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some examples, the ultrasonic receiver 202 may be, or may include, an ultrasonic receiver array. In some examples, the apparatus 200 may include one or more separate ultrasonic transmitter elements. In some such examples, the ultrasonic transmitter(s) may include an ultrasonic plane-wave generator.

The light source system 204 may, in some examples, include an array of light-emitting diodes. In some implementations, the light source system 204 may include one or more laser diodes. According to some implementations, the light source system may include at least one infrared, red, green, blue, white or ultraviolet light-emitting diode. In some implementations, the light source system 204 may include one or more laser diodes. For example, the light source system 204 may include at least one infrared, red, green, blue, white or ultraviolet laser diode. In some implementations, the light source system 204 may include one or more organic LEDs (OLEDs).

In some implementations, the light source system 204 may be configured for emitting various wavelengths of light, which may be selectable in order to achieve greater penetration into biological tissue and/or to trigger acoustic wave emissions primarily from a particular type of material. For example, because near-infrared (near-IR) light is not as strongly absorbed by some types of biological tissue (such as melanin and blood vessel tissues) as relatively shorter wavelengths of light, in some implementations the light source system 204 may be configured for emitting one or more wavelengths of light in the near IR range, in order to obtain photoacoustic emissions from relatively deep biological tissues. In some such implementations the control system 206 may control the wavelength(s) of light emitted by the light source system 204 to be in the range of 750 to 850 nm, e.g., 808 nm. However, hemoglobin does not absorb near-IR light as much as hemoglobin absorbs light having shorter wavelengths, e.g., ultraviolet, violet, blue or green light. Near-IR light can produce suitable photoacoustic emissions from some blood vessels (e.g., 1 mm in diameter or larger), but not necessarily from very small blood vessels. In order to achieve greater photoacoustic emissions from blood in general and from smaller blood vessels in particular, in some implementations the control system 206 may control the wavelength(s) of light emitted by the light source system 204 to be in the range of 495 to 570 nm, e.g., 520 nm or 532 nm. Wavelengths of light in this range are more strongly absorbed by biological tissue and therefore may not penetrate the biological tissue as deeply, but can produce relatively stronger photoacoustic emissions in blood than near-IR light. In some examples the control system 206 may control the wavelength(s) of light emitted by the light source system 204 to preferentially induce acoustic waves in blood vessels, other soft tissue, and/or bones. For example, an infrared (IR) light-emitting diode LED may be selected and a short pulse of IR light emitted to illuminate a portion of a target object and generate acoustic wave emissions that are then detected by the ultrasonic receiver 202. In another example, an IR LED and a red LED or other color such as green, blue, white or ultraviolet (UV) may be selected and a short pulse of light emitted from each light source in turn with ultrasonic images obtained after light has been emitted from each light source. In other implementations, one or more light sources of different wavelengths may be fired in turn or simultaneously to generate acoustic emissions that may be detected by the ultrasonic receiver. Image data from the ultrasonic receiver that is obtained with light sources of different wavelengths and at different depths (e.g., as discussed in detail below) into the target object may be combined to determine the location and type of material in the target object. Image contrast may occur as materials in the body generally absorb light at different wavelengths differently. As materials in the body absorb light at a specific wavelength, they may heat differentially and generate acoustic wave emissions with sufficiently short pulses of light having sufficient intensities. Depth contrast may be obtained with light of different wavelengths and/or intensities at each selected wavelength. That is, successive images may be obtained at a fixed RGD (which may correspond with a fixed depth into the target object) with varying light intensities and wavelengths to detect materials and their locations within a target object. For example, hemoglobin, blood glucose and/ or blood oxygen within a blood vessel inside a target object such as a finger may be detected photoacoustically.

According to some implementations, the light source system 204 may be configured for emitting a light pulse with a pulse width less than about 100 nanoseconds. In some implementations, the light pulse may have a pulse width between about 10 nanoseconds and about 500 nanoseconds or more. According to some examples, the light source system may be configured for emitting a plurality of light pulses at a pulse repetition frequency between 10 Hz and 100 kHz. Alternatively, or additionally, in some implementations the light source system 204 may be configured for emitting a plurality of light pulses at a pulse repetition frequency between about 1 MHz and about 100 MHz. Alternatively, or additionally, in some implementations the light source system 204 may be configured for emitting a plurality of light pulses at a pulse repetition frequency between about 10 Hz and about 1 MHz. In some examples, the pulse repetition frequency of the light pulses may correspond to an acoustic resonant frequency of the ultrasonic receiver and the substrate. For example, a set of four or more light pulses may be emitted from the light source system 204 at a frequency that corresponds with the resonant frequency of a resonant acoustic cavity in the sensor stack, allowing a build-up of the received ultrasonic waves and a higher resultant signal strength. In some implementations, filtered light or light sources with specific wavelengths for detecting selected materials may be included with the light source system 204. In some implementations, the light source system may contain light sources such as red, green and blue LEDs of a display that may be augmented with light sources of other wavelengths (such as IR and/or UV) and with light sources of higher optical power. For example, high-power laser diodes or electronic flash units (e.g., an LED or xenon flash unit) with or without filters may be used for short-term illumination of the target object.

The control system 206 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 206 also may include (and/or be configured for communication with) one or more memory devices, such as one or more random access memory (RAM) devices, read-only memory (ROM) devices, etc. Accordingly, the apparatus 200 may have a memory system that includes one or more memory devices, though the memory system is not shown in FIG. 2. The control system 206 may be configured for receiving and processing data from the ultrasonic receiver 202, e.g., as described below. If the apparatus 200 includes an ultrasonic transmitter, the control system 206 may be configured for controlling the ultrasonic transmitter. In some implementations, functionality of the control system 206 may be partitioned between one or more controllers or processors, such as a dedicated sensor controller and an applications processor of a mobile device.

According to aspects of the disclosure, the control system 206 may be configured to control the light source system 204 and the ultrasonic receiver 202 in order to implement photoacoustic plethysmography (PAPG) for blood pressure prediction. According to various implementations, the control system 206 may control the light source system 204 to cause the light source system 204 to emit light (such as light pulses) of suitable intensities, wavelengths, and pulse repetition frequencies for PAPG-based blood pressure prediction. According to various implementations, the control system 206 may control the ultrasonic receiver 202 to monitor for acoustic waves emitted from human tissue as a result of light emissions of the light source system 204, and detect such acoustic wave emissions when they occur. According to various implementations, the control system 206 may be configured to process signals received from the ultrasonic receiver 202 to obtain PAPG data, based on which it may perform PAPG-based blood pressure prediction.

Some implementations of the apparatus 200 may include the interface system 208. In some examples, the interface system 208 may include a wireless interface system. In some implementations, the interface system 208 may include a user interface system, one or more network interfaces, one or more interfaces between the control system 206 and a memory system and/or one or more interfaces between the control system 206 and one or more external device interfaces (e.g., ports or applications processors).

According to some examples, the apparatus 200 may include a display system 210 that includes one or more displays. For example, the display system 210 may include one or more LED displays, such as one or more organic LED (OLED) displays.

The apparatus 200 may be used in a variety of different contexts, many examples of which are disclosed herein. For example, in some implementations a mobile device may include the apparatus 200. In some implementations, a wearable device may include the apparatus 200. The wearable device may, for example, be a bracelet, an armband, a wristband, a ring, a headband, an carbud or a patch.

Figure 3A:
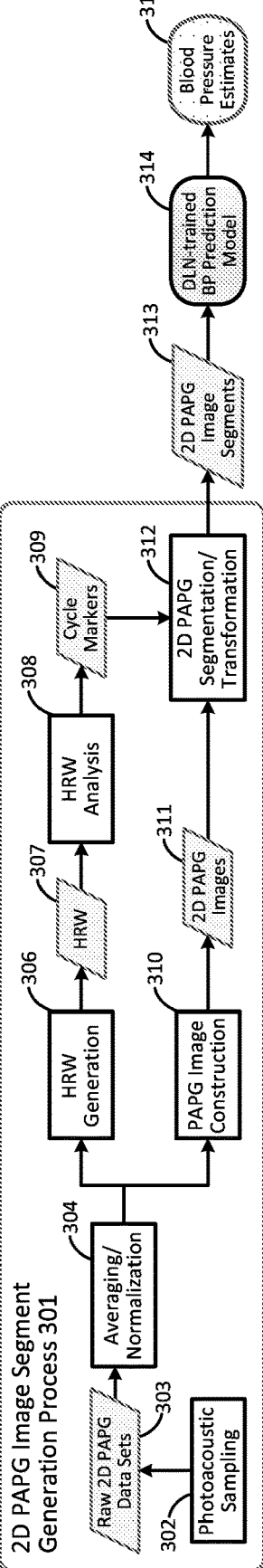
FIG. 3A is a block diagram that illustrates a first example blood pressure estimation process according to some implementations.

FIG. 3A is a block diagram that illustrates an example blood pressure estimation process 300 according to some implementations. Blood pressure estimation process 300 is a 2D PAPG-based blood pressure estimation process, and includes a 2D PAPG image segment generation process 301, which is implemented to generate 2D PAPG image segments 313. According to 2D PAPG image segment generation process 301, photoacoustic sampling is performed at 302 to obtain raw 2D PAPG data sets 303. According to various implementations, the photoacoustic sampling at 302 may be performed using the light source system 204 and ultrasonic receiver 202 of apparatus 200 of FIG. 2. In some implementations, the photoacoustic sampling system 504 of biometric system 500 of FIG. 5 (see below) may perform the photoacoustic sampling at 302. Each raw 2D PAPG data set 303 can include a plurality of raw 2D PAPG data samples. According to aspects of the disclosure, any given raw 2D PAPG data set 303 can be generated by sampling measurements of reflected acoustic waves for an amount of time corresponding to a data collection interval duration (such as 10 seconds, for example). Raw 2D PAPG data sets 303 can be averaged and normalized at 304. According to aspects of the disclosure, the averaging at 304 can involve overlapping sliding-window averaging of data in raw 2D PAPG data sets 303 to reduce an effective underlying light source pulse repetition frequency (PRF) of 2D PAPG data sets 303. For instance, in some examples, data in raw 2D PAPG data sets 303 can reflect a 25 kHz PRF applied for a photoacoustic sampling light source, and overlapping sliding-window averaging can be applied at 304 to reduce the effective underlying light source PRF by a factor of 50, to 500 Hz.

Based on averaged and normalized 2D PAPG data obtained at 304, PAPG image construction can be performed at 310 to create 2D PAPG images 311. 2D PAPG images 311 can depict, over an amount of time corresponding to the data collection interval duration (such as 10 seconds, for example) associated with the raw 2D PAPG data sets 303, the relative amounts of reflected acoustical energy for various depths within human tissue. Any given 2D PAPG image 311 can depict reflected acoustical energies over a time period covering multiple heart rate cycles. At 312, a 2D PAPG segmentation and transformation procedure can be applied to generate 2D PAPG image segments 313 by segmenting and transforming 2D PAPG images 311. Each 2D PAPG image segment 313 can depict reflected acoustical energies over one respective heart rate cycle. In some examples, the 2D PAPG segmentation and transformation procedure can include transforming segments of 2D PAPG images 311 via fast Fourier transform (FFT), wavelet transform, or another suitable type of transform.

2D PAPG image segments 313 can be provided as inputs to a deep-learning network (DLN)-trained blood pressure (BP) prediction model 314. In some examples, DLN-trained blood pressure prediction model 314 can be a implemented as a long short-term memory (LSTM) neural network or a convolutional neural network (CNN). Based on 2D PAPG image segments 313, DLN-trained blood pressure prediction model 314 can generate blood pressure estimates 315. According to aspects of the disclosure, blood pressure estimates 315 can include any or all of systolic blood pressure (SBP) estimate, a diastolic blood pressure (DBP) estimate, and a pulse pressure (PP) estimate. In some examples, DLN-trained blood pressure prediction model 314 can determine one or more predictive factors based on 2D PAPG image segments 313, and can determine blood pressure estimates 315 based at least in part on those predictive factor(s). According to various implementations, such predictive factor(s) can include direct or indirect indicators of properties such as systolic artery diameter, diastolic artery diameter, arterial distention, arterial strain, arterial wave velocity (AWV), and pulse wave velocity (PWV).

Averaged and normalized 2D PAPG data obtained at 304 can also be passed to a heart rate waveform (HRW) generation procedure at 306, which can generate heart rate waveforms 307 based on the averaged and normalized 2D PAPG data. According to aspects of the disclosure, the heart rate waveform generation procedure at 306 can include extracting HRW data from the averaged and normalized 2D PAPG data obtained at 304 and bandpass filtering the HRW data. The heart rate waveforms 307 can be subjected to heart rate waveform analysis at 308 to identify cycle markers 309, which can indicate boundaries between portions of heart rate waveforms 307 corresponding to different heart rate cycles. According to aspects of the disclosure, these cycle markers 309 can serve as bases for segmenting 2D PAPG images 311 in conjunction with the 2D PAPG segmentation and transformation procedure at 312. In some implementations, control system 206 of apparatus 200 of FIG. 2 may perform the operations at 304, 306, 308, 310, 312, and 314 in blood pressure estimation process 300. In some implementations, control system 502 of biometric system 500 of FIG. 5 (see below) may perform these operations.

Figure 3B:
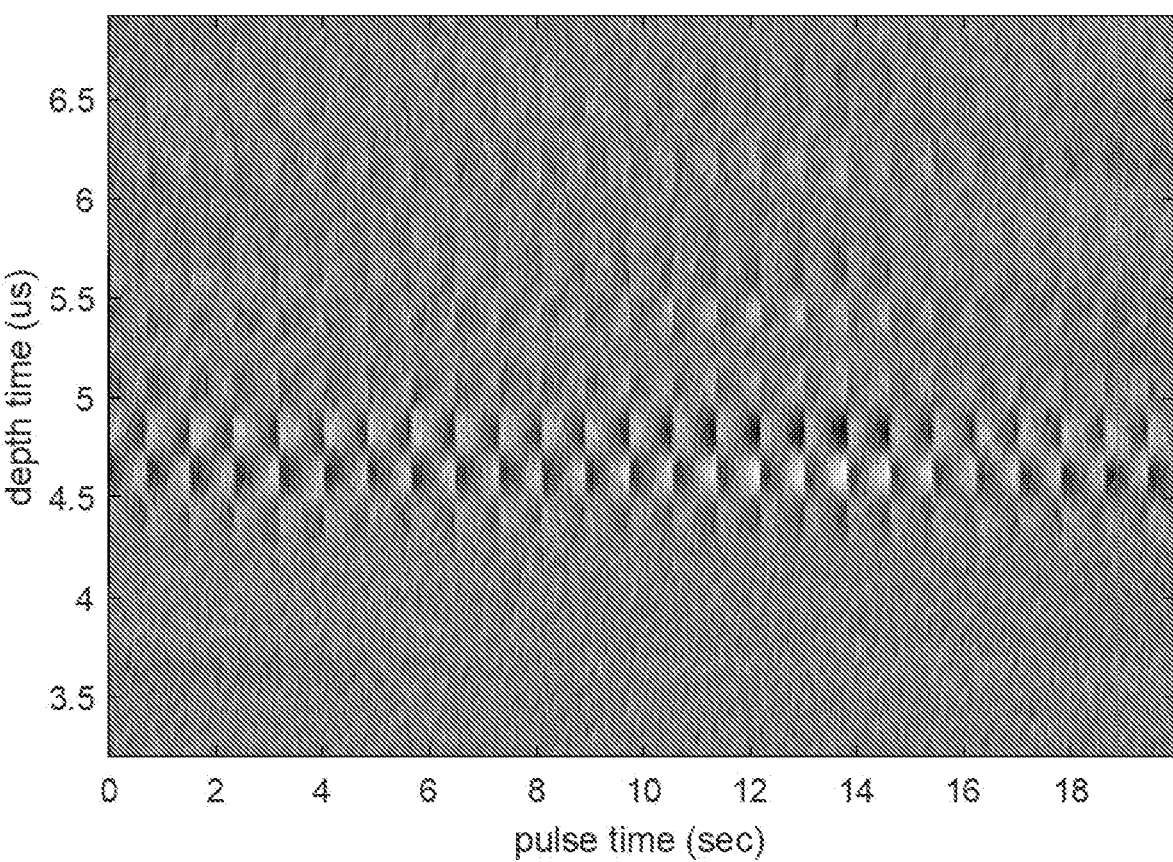
FIG. 3B illustrates an example plethysmography image according to aspects of the disclosure.

FIG. 3B depicts an example plethysmography image 350 according to aspects of the disclosure. Plethysmography image 350 may be representative of, for instance, a 2D PAPG image 311 constructed in conjunction with implementation of blood pressure estimation scheme 300 of FIG. 3A according to some examples. A horizontal axis provides scale for a pulse time dimension of plethysmography image 350 (in units of seconds in the depicted example). A vertical axis provides scale for a depth time dimension of plethysmography image 350 (in units of microseconds ($\mu$s) in the depicted example). The depth time dimension can represent arterial diameter, distension, and strain, while the pulse time dimension can represent arterial wave velocity (AWV) and pulse wave velocity (PWV). The intensity at a given point in plethysmography image 350 can correspond to an amount of acoustic energy proportional to an amount of light absorbed by arterial hemoglobin.

Figure 4A:
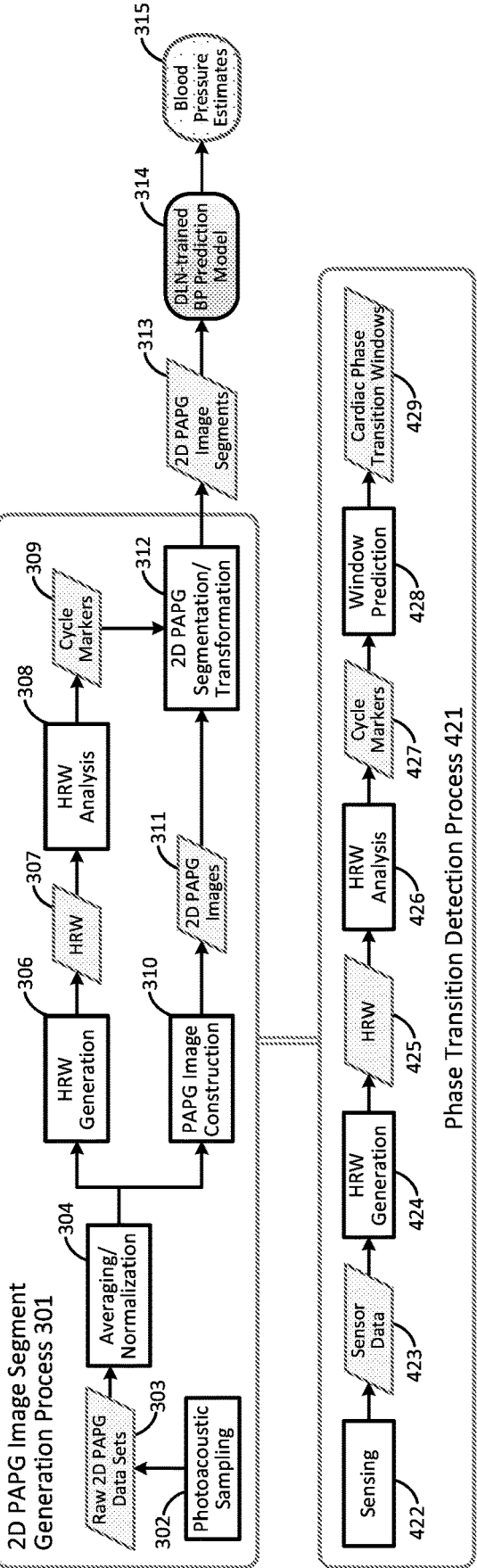
FIG. 4A is a block diagram that illustrates a second example blood pressure estimation process according to some implementations.

FIG. 4A is a block diagram that illustrates an example blood pressure estimation process 400 according to some implementations. Like blood pressure estimation process 300 of FIG. 3A, blood pressure estimation process 400 is a 2D PAPG-based blood pressure estimation process. However, according to blood pressure estimation process 400, photoacoustic sampling can be performed selectively, so as to obtain 2D PAPG imagery corresponding to portions of the subject's heart rate cycle that are of significance with respect to 2D PAPG-based blood pressure prediction while refraining from raw 2D PAPG data capture and processing with respect to portions of the heart rate cycle that are not of significance. According to aspects of the disclosure, the significant portions of the heart rate cycle can correspond to cardiac phase transition windows representing time intervals during which cardiac phase transitions—such as systolic-to-diastolic transitions, diastolic-to-systolic transitions, or both—occur.

According to blood pressure estimation process 400, a phase transition detection process 421 is used to identify cardiac phase transition windows 429, and the photoacoustic sampling at 302 is activated at the beginnings of the cardiac phase transition windows 429 and deactivated by the ends of the cardiac phase transition windows 429. In some implementations, phase transition detection process 421 can be a non-PAPG-based procedure operating in parallel with 2D PAPG image segment generation process 301. In some implementations, for example, phase transition detection process 421 may be a photoplethysmography (PPG)-based process.

According to phase transition detection process 421, sensing can be performed at 422 to obtain sensor data 423 that is suitable as a basis for heart rate waveform generation. In some implementations, biometric sensor 522 of biometric system 500 of FIG. 5 (see below) may perform the sensing at 422 to obtain sensor data 423. In some implementations, the sensing at 422 can be performed using a PPG sensor, and sensor data 423 can be PPG data. Via a heart rate waveform generation procedure at 424, a heart rate waveform 425 can be generated based on the sensor data 423. The heart rate waveform 425 can be subjected to heart rate waveform analysis at 426 to identify cycle markers 427, which can indicate boundaries between portions of heart rate waveforms 425 corresponding to different heart rate cycles. A window prediction procedure at 428 can determine or predict cardiac phase transition windows 429 based on the identified cycle markers 427.

In some implementations, control system 206 of apparatus 200 of FIG. 2 may perform the operations at 424, 426, and 428 in blood pressure estimation process 400. In some other implementations, control system 206 may perform some of the operations at 424, 426, and 428, and a second control system—possibly executing on a device separate to apparatus 200—may perform other(s) of the operations at 424, 426, and 428, or such a second control system may perform all of the operations at 424, 426, and 428. In some implementations, heart rate waveform generator 524 of biometric system 500 of FIG. 5 (see below) may perform the operations at 424, and heart rate waveform analyzer 426 may perform the operations at 426 and 428.

Figure 4B:
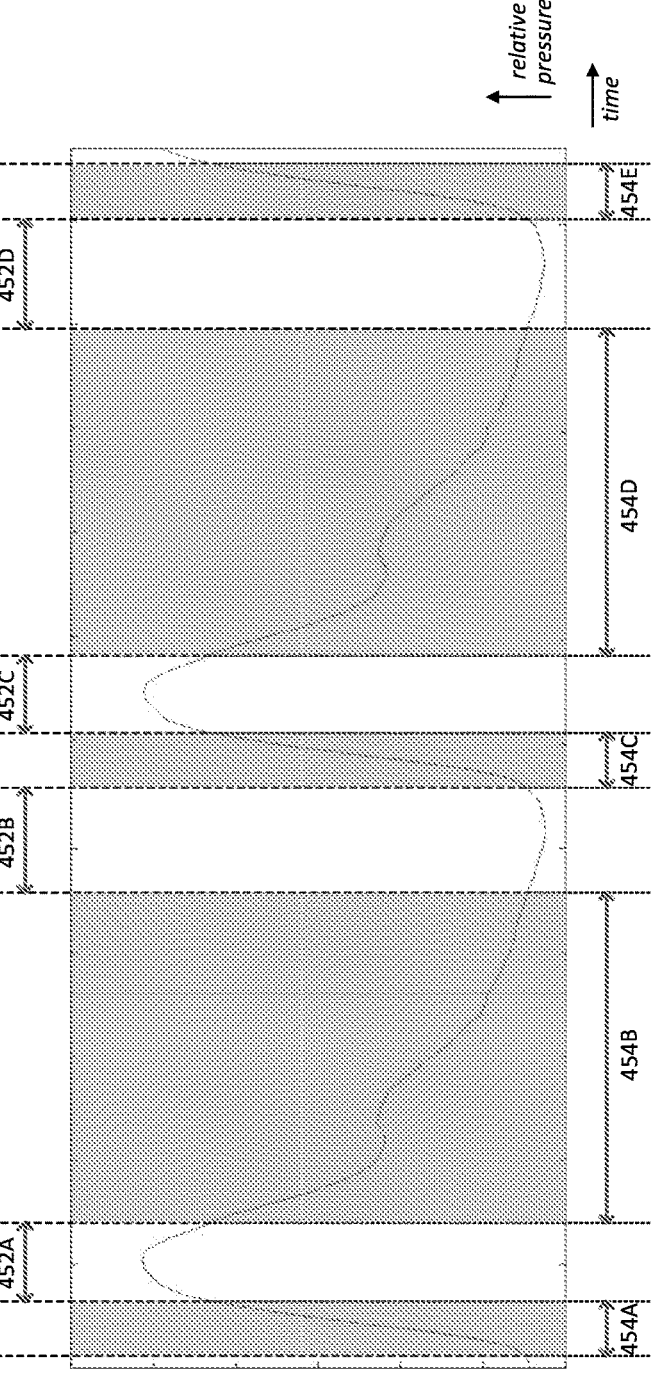
FIG. 4B illustrates example cardiac phase transition windows associated with a heart rate waveform.

FIG. 4B illustrates example cardiac phase transition windows associated with a heart rate waveform 450. Two heart rate cycles of heart rate waveform 450 are shown in FIG. 4B. The horizontal dimension represents time, and the vertical dimension represents relative pressure. Four cardiac phase transition windows 452A, 452B, 452C, and 452D are shown, each of which represents a time interval spanning from shortly before to shortly after the relative pressure reaches a peak or trough. Cardiac phase transition windows 452A and 452C, which span from times $t_2$-$t_3$ and $t_6$-$t_7$, respectively, correspond to systolic-to-diastolic transitions, and contain relative pressure peaks. Cardiac phase transition windows 452B and 452D, which span from times $t_4$-$t_5$ and $t_8$-$t_9$, respectively, correspond to diastolic-to-systolic transitions, and contain relative pressure troughs.

With respect to 2D PAPG-based blood pressure estimation according to blood pressure estimation process 400 of FIG. 4A, data of significant predictive value may largely reside within cardiac phase transition windows 452A, 452B, 452C, and 452D, which may constitute examples of the cardiac phase transition windows 429 in FIG. 4A. Data residing in the regions 454A, 454B, 454C, 454D, and 454E (shaded in gray) outside cardiac phase transition windows 452A, 452B, 452C, and 452D may be of less significance, such that data residing in 454A, 454B, 454C, 454D, and 454E can be omitted from consideration without meaningfully impacting the accuracy of 2D PAPG-based blood pressure estimation. In conjunction with blood pressure estimation process 400 of FIG. 4A, photoacoustic sampling may be activated at the respective beginnings of cardiac phase transition windows 452A, 452B, 452C, and 452D, and deactivated by the respective ends of cardiac phase transition windows 452A, 452B, 452C, and 452D.

Figure 5:
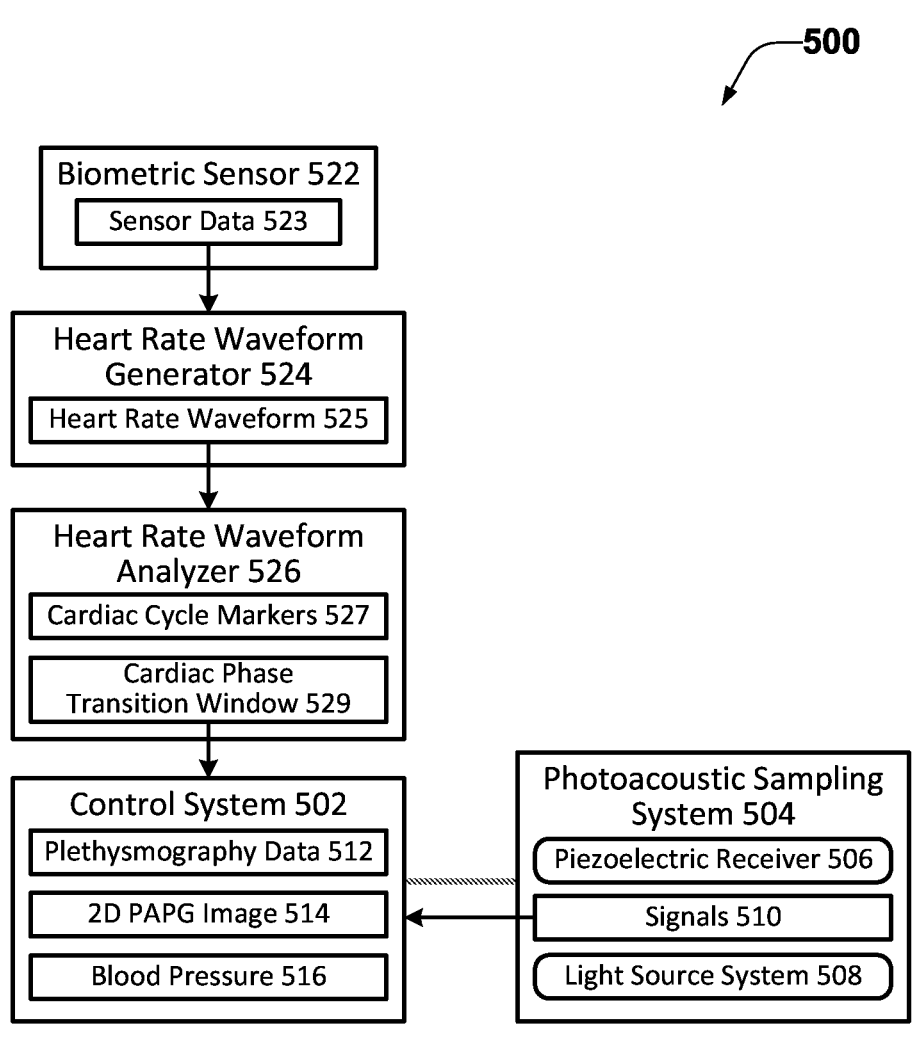
FIG. 5 illustrates an example biometric system according to aspects of the disclosure.

FIG. 5 illustrates an example biometric system 500 according to aspects of the disclosure. Biometric system 500 may be representative of a system that can implement blood pressure estimation process 400 of FIG. 4A. Biometric system 500 can include a control system 502, a heart rate waveform analyzer 526, and a photoacoustic sampling system 504. The photoacoustic sampling system 504 may include a piezoelectric receiver 506 and a light source system 508. The heart rate waveform analyzer 526 can be configured to monitor a heart rate waveform 525 associated with a subject to detect cardiac cycle markers 527, and determine a cardiac phase transition window 529 based on the cardiac cycle markers. According to aspects of the disclosure, the heart rate waveform analyzer 526 can perform operations corresponding to the heart rate waveform analysis at 426 and window prediction at 428 in FIG. 4A, and cycle markers 527 and cardiac phase transition window 529 can correspond to cycle markers 427 and cardiac phase transition window 429, respectively.

According to aspects of the disclosure, cardiac cycle markers 527 may indicate timings of observed cardiac phase transitions, and heart rate waveform analyzer may apply a prediction model to determine cardiac phase transition window 529 based on the timings of the observed cardiac phase transitions. In some examples, cardiac phase transition window 529 may correspond to a systolic-to-diastolic transition. In other examples, cardiac phase transition window 529 may correspond to a diastolic-to-systolic transition.

In some implementations, biometric system 500 can include a biometric sensor 522 configured to generate sensor data 523 that is suitable as a basis for heart rate waveform generation, and can include a heart rate waveform generator

524 configured to generate heart rate waveform 525 based on the sensor data 523. In some examples, biometric sensor 522 can be a heart activity sensor, such as a PPG sensor, an electrocardiogram (ECG) sensor, a contact microphone used for sensing heart activity, or another type of device capable of sensing heart activity such as heart beats. In some examples, for instance, biometric sensor 522 can be a PPG sensor and sensor data 523 can be PPG data, such as may be comprised in a PPG data stream.

In some implementations, heart rate waveform generator 524 and heart rate waveform analyzer 526 may both reside on a same device as control system 502 and photoacoustic sampling system 504. In some implementations, biometric sensor 522 may be external to that device, while in other implementations, biometric sensor 522 may also reside on that device. In some implementations, one or both of heart rate waveform generator 524 and heart rate waveform analyzer 526 can be a subsystem of control system 502. In some implementations, one or both of heart rate waveform generator 524 and heart rate waveform analyzer 526 can correspond to functionality external to control system 502. In some such implementations, such functionality may reside on a device separate from that hosting control system 502. In an example, biometric sensor 522, heart rate waveform generator 524, and heart rate waveform analyzer 526 may reside on a PPG blood pressure estimation device that is communicatively coupled with a device that hosts control system 502 and photoacoustic sampling system 504.

According to aspects of the disclosure, control system 502 can generally be configured to control the photoacoustic sampling system 504 to cause it to perform photoacoustic sampling within cardiac phase transition windows and refrain from photoacoustic sampling outside of cardiac phase transition windows. In this context, control system 502 can activate photoacoustic sampling system 504 at a start of cardiac phase transition window 529.

During the cardiac phase transition window 529, control system 502 can control light source system 508 to cause light source system 508 to emit plurality of light pulses into biological tissue of the subject. The biological tissue can include blood and blood vessels at depths within the biological tissue. The control system 502 can receive, from piezoelectric receiver 506, signals 510 corresponding to acoustic waves emitted from portions of the biological tissue of the subject. The acoustic waves can correspond to photoacoustic emissions from the blood and the blood vessels caused by the plurality of light pulses.

In some implementations, control system 502 can obtain plethysmography data 512 based on the received signals 510, and can determine a blood pressure 516 based on the plethysmography data 512. Blood pressure 516 can include any or all of a systolic blood pressure, a diastolic blood pressure, and a pulse pressure. In some implementations, control system 502 can determine blood pressure 516 based on systolic phase data comprised in plethysmography data 512, without reference to diastolic phase data comprised in plethysmography data 512. In some implementations, control system 502 can be configured to display the blood pressure 516 on a display.

According to some implementations, plethysmography data 512 can be PAPG data, and control system 502 can generate a 2D PAPG image 514 based on plethysmography data 512 and determine blood pressure 516 based on 2D PAPG image 514. In some examples, 2D PAPG image 514 may comprise a depth time dimension and a pulse time dimension. In some examples, control system 502 may use a blood pressure prediction model trained using a deep learning network (DLN), such as a long short-term memory (LSTM) neural network or a convolutional neural network, to determine blood pressure 516 based on 2D PAPG image 514.

According to aspects of the disclosure, control system 502 can deactivate photoacoustic sampling system 504 by an end of cardiac phase transition window 529. In some examples, control system 504 can deactivate photoacoustic sampling system 504 prior to the end of cardiac phase transition window 529 responsive to a determination, prior to the end of cardiac phase transition window 529, that plethysmography data 512 includes at least a threshold number of samples. In some other examples, control system 502 can deactivate photoacoustic sampling system 504 at the end of cardiac phase transition window 529 responsive to a determination that the end of cardiac phase transition window 529 has been reached.

FIG. 6 illustrates an example method 600 according to aspects of the disclosure. Method 600 may be representative of operations that may, for instance, be performed by biometric system 500 of FIG. 5 in conjunction with implementation of blood pressure estimation scheme 400 of FIG. 4A according to some examples. In various implementations, method 600 may include more or fewer blocks than indicated. Moreover, the blocks of method 600 are not necessarily performed in the order indicated. In some instances, one or more of the blocks shown in FIG. 6 may be performed concurrently.

According to method 600, a heart rate waveform associated with a subject may be monitored at 605 to detect cardiac cycle markers. For example, heart rate waveform analyzer 526 of biometric system 500 of FIG. 5 may monitor a heart rate waveform 525 associated with a subject to detect cardiac cycle markers 527. In some examples, the heart rate waveform may be obtained based on a data stream received from a heart activity sensor. For example, heart rate waveform analyzer 526 of biometric system 500 of FIG. 5 may receive heart rate waveform 525 from heart rate waveform generator 524, which may generate heart rate waveform 525 based on sensor data 523 received from biometric sensor 522, sensor data 523 may be a data stream output by biometric sensor 522, and biometric sensor 522 may be a PPG sensor, ECG sensor, a contact microphone used for sensing heart activity, or another type of device capable of sensing heart activity such as heart beats.

At 610, a cardiac phase transition window may be determined based on the cardiac cycle markers. For example, heart rate waveform analyzer 526 of biometric system 500 of FIG. 5 may determine a cardiac phase transition window 529 based on cardiac cycle markers 527. According to aspects of the disclosure, the cardiac cycle markers may indicate timings of observed cardiac phase transitions, and a prediction model may be used to determine the cardiac phase transition window based on the timings of the observed cardiac phase transitions. In some examples, the cardiac phase transition window may correspond to a systolic-to-diastolic transition. In other examples, the cardiac phase transition window may correspond to a diastolic-to-systolic transition. At 615, a photoacoustic sampling system may be activated at a start of the cardiac phase transition window. The photoacoustic sampling system may include a piezoelectric receiver and a light source system. For example, control system 502 of biometric system 500 of FIG. 5 may activate photoacoustic sampling system 504 at a start of cardiac phase transition window 529, and photoacoustic sampling system 505 may include piezoelectric receiver 506 and light source system 508.

During the cardiac phase transition window determined at 610, operations may be performed at 620, 625, and 630. At 620, the light source system can be controlled to emit a plurality of light pulses into biological tissue of the subject. For example, control system 502 of biometric system 500 of FIG. 5 may control light source system 508 to emit a plurality of light pulses into biological tissue of the subject. According to aspects of the disclosure, the biological tissue may include blood and blood vessels at depths within the biological tissue. At 625, signals may be received from the piezoelectric receiver that correspond to acoustic waves emitted from portions of the biological tissue. For example, control system 502 of biometric system 500 of FIG. 5 may receive, from piezoelectric receiver 506, signals 510 that correspond to acoustic waves emitted from portions of the biological tissue.

At 630, plethysmography data may be obtained based on the signals. For example, control system 502 of biometric system 500 of FIG. 5 may obtain plethysmography data 512 based on signals 510 received from piezoelectric receiver 506 of photoacoustic sampling system 504. In some examples, a blood pressure may be determined based on the plethysmography data. For example, control system 502 of biometric system 500 of FIG. 5 may determine blood pressure 516 based on plethysmography data 512. According to aspects of the disclosure, the determined blood pressure may include any or all of a systolic blood pressure, a diastolic blood pressure, and a pulse pressure. In some examples, the blood pressure may be displayed on a display. For example, control system 502 of biometric system 500 of FIG. 5 may display blood pressure 516 on a display. In some examples, the blood pressure may be determined based on systolic phase data comprised in the plethysmography data, without reference to diastolic phase data comprised in the plethysmography data. For example, control system 502 of biometric system 500 of FIG. 5 may determine blood pressure 516 based on systolic phase data comprised in plethysmography data 512, without reference to diastolic phase data comprised in plethysmography data 512.

In some examples, the plethysmography data obtained at 630 may be photoacoustic plethysmography (PAPG) data. In some examples, a two-dimensional (2D) PAPG image may be generated based on the PAPG data. In some examples, the 2D PAPG image may comprise a depth time dimension and a pulse time dimension. In some examples, a blood pressure may be determined based on the 2D PAPG image. For example, control system 502 of biometric system 500 of FIG. 5 may generate a 2D PAPG image 514 based on plethysmography data 512 that comprises PAPG data, and may determine blood pressure 516 based on the 2D PAPG image 514. In some examples, a blood pressure prediction model trained using a deep learning network (DLN), such as a long short-term memory (LSTM) neural network or a convolutional neural network may be used to determine the blood pressure based on the 2D PAPG image. For example, control system 502 of biometric system 500 of FIG. 5 may determine blood pressure 516 based on a 2D PAPG image 514 generated based on plethysmography data 512 comprising PAPG data, using a blood pressure prediction model trained using a deep learning network (DLN) such as an LSTM neural network or convolutional neural network. In some examples, the 2D PAPG image may comprise a depth time dimension and a pulse time dimension.

At 635, the photoacoustic sampling system may be deactivated by an end of the cardiac phase transition window. For example, control system 502 of biometric system 500 of FIG. 5 may deactivate photoacoustic sampling system 504 by an end of cardiac phase transition window 529. In some examples, the photoacoustic sampling system can be deactivated prior to the end of the cardiac phase transition window responsive to a determination, prior to the end of the cardiac phase transition window, that the plethysmography data includes at least a threshold number of samples. In some other examples, the photoacoustic sampling system can be deactivated at the end of the cardiac phase transition window responsive to a determination that the end of the cardiac phase transition window has been reached.

Figure 7A:
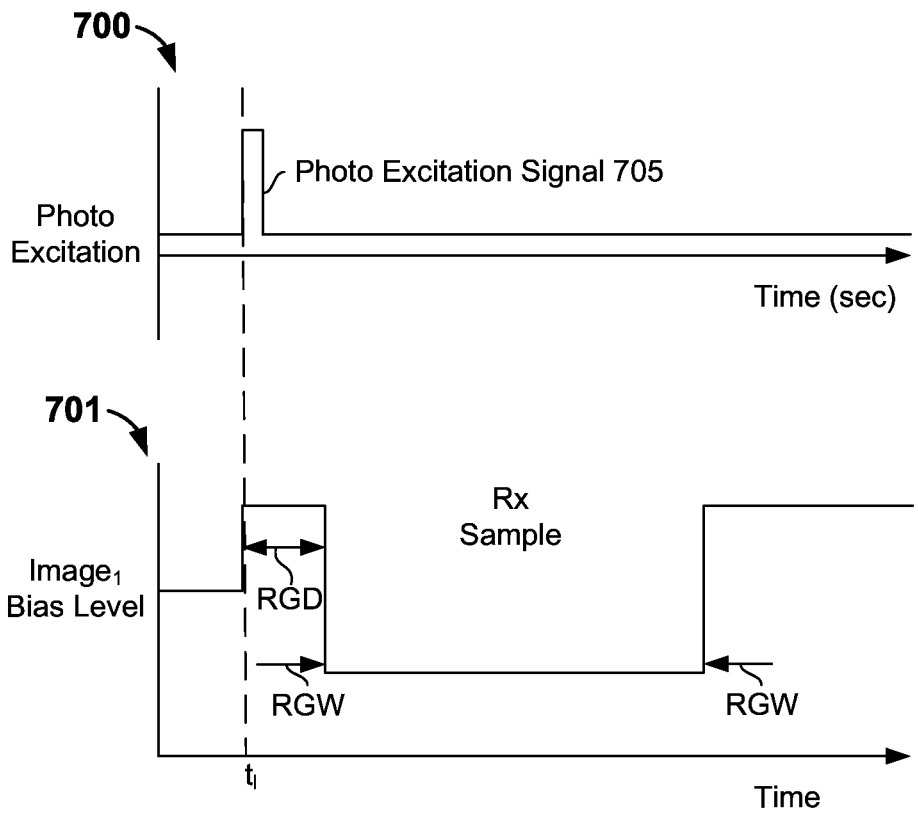
FIG. 7A shows an example of a range-gate window (RGW) selected to receive acoustic waves emitted from a range of different depths.

According to aspects of the disclosure, a biometric system such as biometric system 500 of FIG. 5 may be configured for discriminating between vein heart rate waveforms and artery heart rate waveforms by obtaining depth-discriminated signals. FIG. 7A shows an example of a range-gate window (RGW) selected to receive acoustic waves emitted from a range of different depths. The acquisition time delay or range gate delay (which is labeled "RGD" in FIG. 7B) is measured from the beginning time $t_1$ of the photo-excitation signal 705 shown in graph 700. The RGD may, for example, be selected to correspond with the time required for photoacoustic emissions from a shallowest target of interest to reach a receiver, e.g., as described below with reference to FIGS. 8A and 8B. Accordingly, the RGD may depend on the particular arrangement of the apparatus being used to receive the photoacoustic emissions, including the thickness of the layer(s) between the target object and the receiver and the speed of sound of the layer(s) between the target object and the receiver. The graph 701 depicts a time after RGD during which emitted acoustic waves may be received and sampled by an ultrasonic receiver during an acquisition time window (also known as a range-gate window or a range-gate width) of RGW. In some implementations, the RGW may be 10 microseconds. Other implementations may have larger or smaller RGWs.

In some examples, depth-discriminated signals may be obtained by a process of partitioning the acoustic waves received during the RGW into a plurality of smaller time windows. Each of the time windows may correspond to a depth range inside the target object from which the acoustic waves are received. In some examples, the depth range or thickness of each layer may be 0.5 mm. Assuming a speed of sound of 1.5 mm/microsecond, each 0.5 mm layer would correspond to a time slot of approximately 0.33 microseconds. However, the depth range may vary according to the particular implementation.

According to some alternative examples, receiving the signals from the piezoelectric receiver involves obtaining depth-discriminated signals by applying first through $N^{th}$ acquisition time delays and receiving first through $N^{th}$ signals during first through $N^{th}$ acquisition time windows, each of the first through $N^{th}$ acquisition time windows occurring after a corresponding one of the first through $N^{th}$ acquisition time delays, wherein N is an integer greater than one. The control system may be configured for determining the first subset of detected heart rate waveforms and the second subset of detected heart rate waveforms based, at least in part, on the depth-discriminated signals.

Figure 7B:
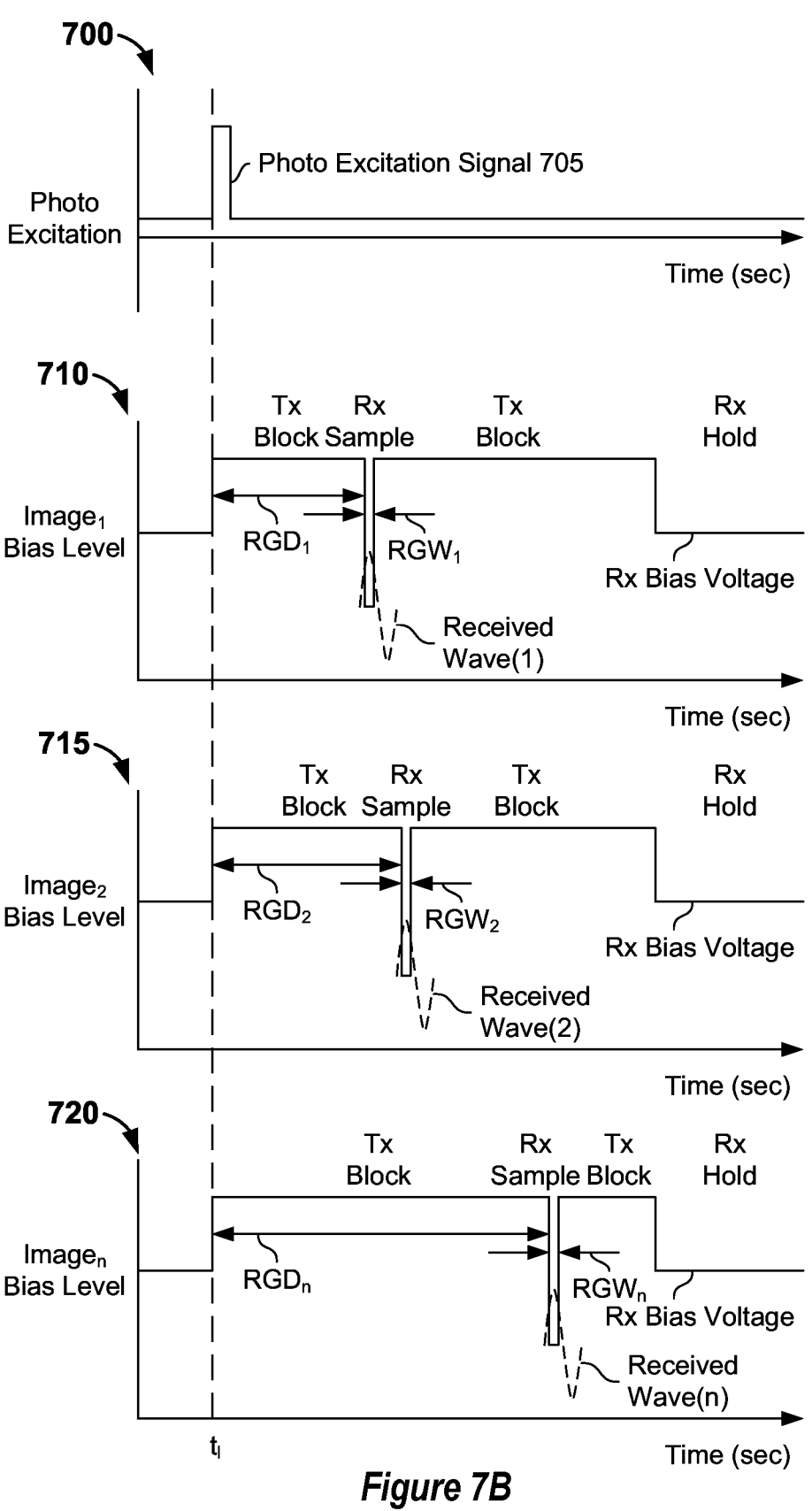
FIG. 7B shows examples of multiple acquisition time delays being selected to receive acoustic waves emitted from different depths.

FIG. 7B shows examples of multiple acquisition time delays being selected to receive acoustic waves emitted from different depths. In these examples, each of the acquisition time delays (which are labeled range-gate delays or RGDs in FIG. 7B) is measured from the beginning time $t_1$ of the photo-excitation signal 705 shown in graph 700. The graph 710 depicts emitted acoustic waves (received wave (1) is one example) that may be received by an ultrasonic sensor array at an acquisition time delay $RGD_1$ and sampled during an acquisition time window (also known as a range-gate window or a range-gate width) of $RGW_1$. Such acoustic waves will generally be emitted from a relatively shallower portion of a target object proximate, or positioned upon, a platen of the biometric system.

Graph 715 depicts emitted acoustic waves (received wave (2) is one example) that are received by the ultrasonic sensor array at an acquisition time delay $RGD_2$ (with $RGD_2 > RGD_1$) and sampled during an acquisition time window of $RGW_2$. Such acoustic waves will generally be emitted from a relatively deeper portion of the target object.

Graph 720 depicts emitted acoustic waves (received wave (n) is one example) that are received at an acquisition time delay $RGD_n$ (with $RGD_n > RGD_2 > RGD_1$) and sampled during an acquisition time window of $RGW_n$. Such acoustic waves will generally be emitted from a still deeper portion of the target object. Range-gate delays are typically integer multiples of a clock period. A clock frequency of 128 MHz, for example, has a clock period of 7.8125 nanoseconds, and RGDs may range from under 10 nanoseconds to over 2000 nanoseconds. Similarly, the range-gate widths may also be integer multiples of the clock period, but are often much shorter than the RGD (e.g. less than about 50 nanoseconds) to capture returning signals while retaining good axial resolution. In some implementations, the acquisition time window (e.g. RGW) may be between 175 nanoseconds to 320 nanoseconds or more. In some examples, the RGW may be more or fewer nanoseconds, e.g., in the range of 25 nanoseconds to 1000 nanoseconds.

Figure 8A:
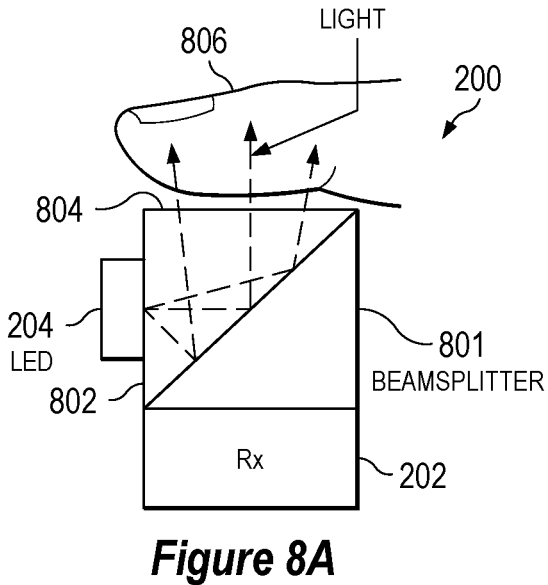
FIGS. 8A and 8B show examples of an apparatus configured to receive acoustic waves emitted from different depths.
Figure 8B:
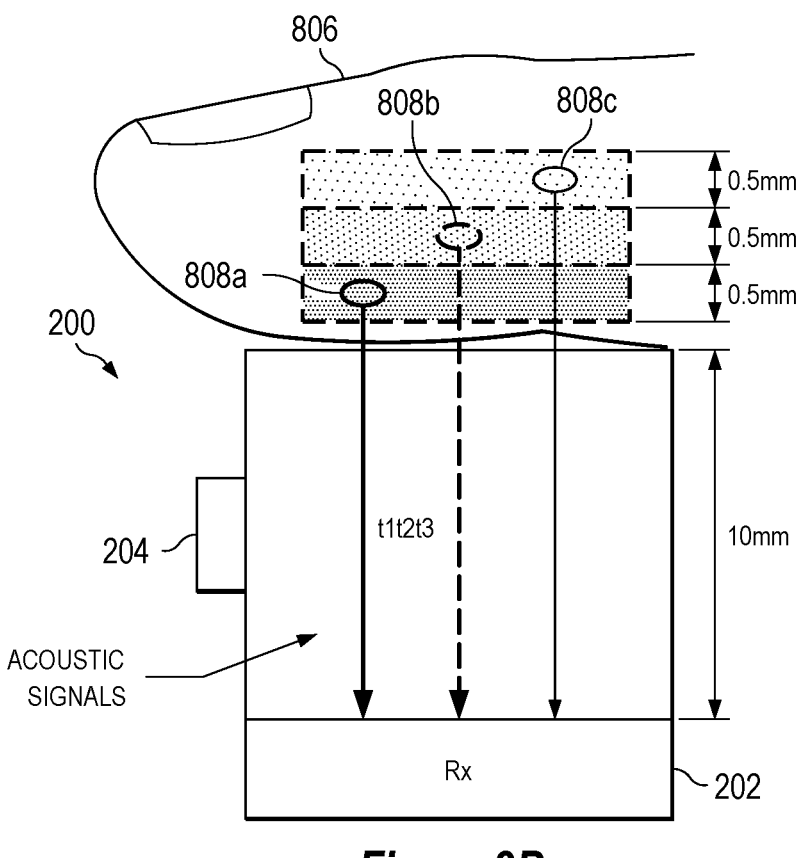

FIGS. 8A and 8B show examples of an apparatus configured to receive acoustic waves emitted from different depths. The apparatus shown in FIGS. 8A and 8B is an example of the apparatus 200 that is shown in FIG. 2. As with the other implementations shown and described herein, the types of elements, the arrangement of the elements and the dimensions of the elements illustrated in FIGS. 8A and 8B are merely shown by way of example.

According to this example, the apparatus 200 includes an ultrasonic receiver 202, a light source system 204 (which includes an LED in this example) and a control system (which is not shown in FIGS. 8A and 8B). According to this implementation, the apparatus 200 includes a beamsplitter 801 onto a side 802 to which the LED is mounted. In this instance, a finger 806 rests upon an adjacent side 804 of the beamsplitter 801.

FIG. 8A shows light emitted from the light source system 204, part of which is reflected by the beamsplitter 801 and enters the finger 806. The range gate delay for this implementation and other implementations may, for example, be selected to correspond with the time required for photoacoustic emissions from a shallowest target of interest to reach a receiver. For example, in one configuration of the apparatus 200 which uses a 12.7 mm beamsplitter between the finger 806 and the ultrasonic receiver 202 (RX in FIG. 8A), the finger surface signal will arrive at the time it takes the acoustic waves to travel through the entire beamsplitter. Using the speed of sound of borosilicate glass of 5500 m/s as an approximate speed of sound for the beamsplitter and with the beamsplitter size of 12.7 mm, this time becomes 12.7 mm/5500 m/s or 2.3 us. Therefore, a range gate delay of 2.3 μs corresponds to the surface of the finger 806. To travel 1 mm into the finger 806, for example, using the speed of sound for tissue now of 1.5 mm/us, this time becomes 1 mm/1.5 mm/μs or ~0.67 μs. Therefore, a range gate delay of ~2.97 μs (2.3 μs+0.67 μs) would cause the ultrasonic receiver 202 to begin sampling acoustic waves reflected from a depth of approximately 1 mm below the outer surface of the finger 806.

FIG. 8B shows acoustic signals corresponding to photoacoustic emissions from tissues (e.g., blood and blood vessels) inside the finger 806, caused by the light that entered the finger 806. In the example shown in FIG. 8B, the acoustic signals originate from different depths (depths 808a, 808b and 808c) within the finger 806. Accordingly, the travel times t1, t2 and t3, from the depths 808a, 808b and 808c, respectively, to the ultrasonic receiver 202, are also different: in this instance, t3>t2>t1. Therefore, multiple acquisition time delays may be selected to receive acoustic waves emitted from the depths 808a, 808b and 808c, e.g., as shown in FIG. 7B and described above.

Figure 9:
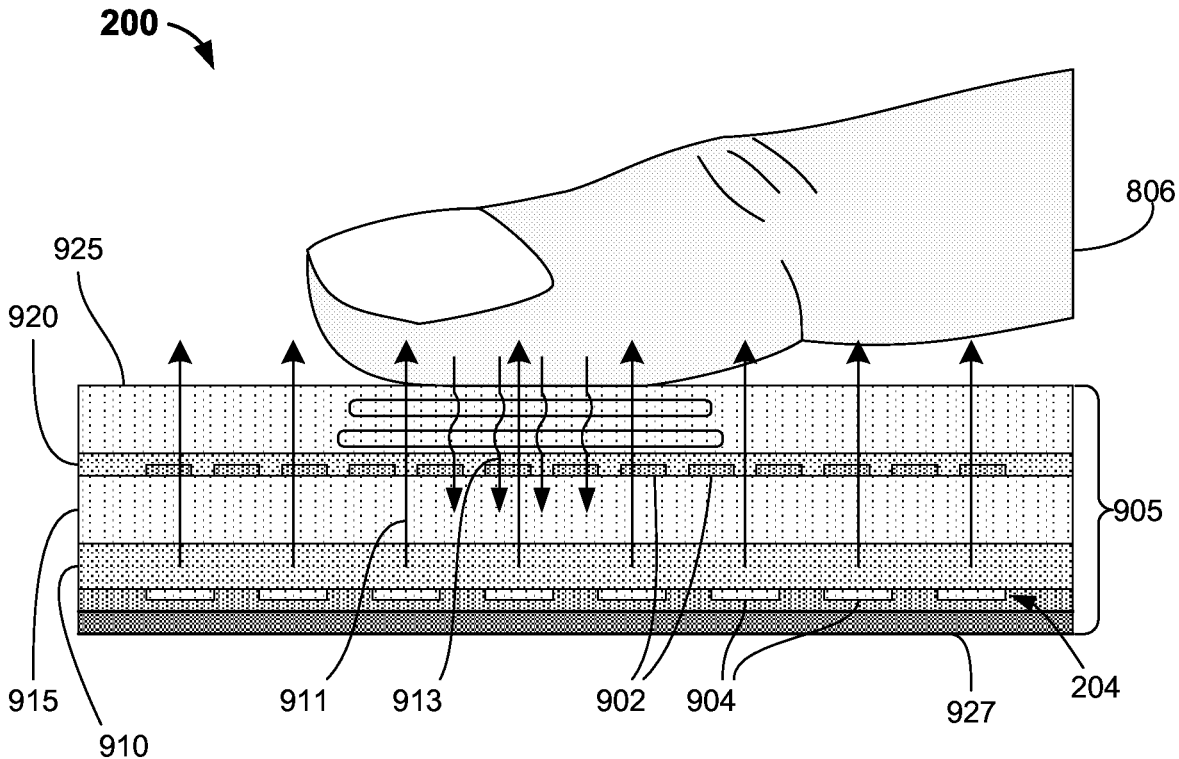
FIG. 9 shows an example of a cross-sectional view of an apparatus capable of performing the method of FIG. 6.

FIG. 9 shows an example of a cross-sectional view of an apparatus capable of performing the method of FIG. 5. The apparatus 200 shown in FIG. 9 is another example of the apparatus 200 that is described above with reference to FIG. 2. As with the other implementations shown and described herein, the types of elements, the arrangement of the elements and the dimensions of the elements illustrated in FIG. 9 are merely shown by way of example.

FIG. 9 shows an example of a target object (the finger 806, in this instance) being illuminated by incident light and subsequently emitting acoustic waves. In this example, the apparatus 200 includes a light source system 204, which may include an array of light-emitting diodes and/or an array of laser diodes. In some implementations, the light source system 204 may be capable of emitting various wavelengths of light, which may be selectable to trigger acoustic wave emissions primarily from a particular type of material. In some instances, the incident light wavelength, wavelengths and/or wavelength range(s) may be selected to trigger acoustic wave emissions primarily from a particular type of material, such as blood, blood vessels, other soft tissue, or bones. To achieve sufficient image contrast, light sources 904 of the light source system 204 may need to have a higher intensity and optical power output than light sources generally used to illuminate displays. In some implementations, light sources with light output of 1-100 millijoules or more per pulse, e.g., 10 millijoules per pulse, with pulse widths in the range of 100 nanoseconds to 600 nanoseconds, may be suitable. In some implementations, the pulse width of the emitted light may be between 10 nanoseconds and 700 nanoseconds.

In this example, incident light 911 has been transmitted from the light sources 904 of the light system 204 through a sensor stack 905 and into an overlying finger 806. The various layers of the sensor stack 905 may include one or more substrates of glass or other material such as plastic or sapphire that is substantially transparent to the light emitted by the light source system 204. In this example, the sensor stack 905 includes a substrate 910 to which the light source system 204 is coupled, which may be a backlight of a display according to some implementations. In alternative implementations, the light source system 204 may be coupled to a front light. Accordingly, in some implementations the light source system 204 may be configured for illuminating a display and the target object.

In this implementation, the substrate 910 is coupled to a thin-film transistor (TFT) substrate 915 for the ultrasonic receiver 202, which includes an array of sensor pixels 902 in this example. According to this example, a piezoelectric receiver layer 920 overlies the sensor pixels 902 of the ultrasonic receiver 202 and a platen 925 overlies the piezoelectric receiver layer 920. Accordingly, in this example the apparatus 200 is capable of transmitting the incident light 911 through one or more substrates of the sensor stack 905 that include the ultrasonic receiver 202 with substrate 915 and the platen 925 that may also be viewed as a substrate. In some implementations, sensor pixels 902 of the ultrasonic receiver 202 may be transparent, partially transparent or substantially transparent, such that the apparatus 200 may be capable of transmitting the incident light 911 through elements of the ultrasonic receiver 202. In some implementations, the ultrasonic receiver 202 and associated circuitry may be formed on or in a glass, plastic or silicon substrate.

According to some implementations, the apparatus 200 may include an ultrasonic transmitter 927, such as the ultrasonic transmitter 927 that is shown in FIG. 9. The ultrasonic transmitter may or may not be part of the ultrasonic receiver 202, depending on the particular implementation. In some examples, the ultrasonic receiver 202 may include PMUT or CMUT elements that are capable of transmitting and receiving ultrasonic waves, and the piezoelectric receiver layer 920 may be replaced with an acoustic coupling layer. In some examples, the ultrasonic receiver 202 may include an array of pixel input electrodes and sensor pixels formed in part from TFT circuitry, an overlying piezoelectric receiver layer 920 of piezoelectric material such as PVDF or PVDF-TrFE, and an upper electrode layer positioned on the piezoelectric receiver layer sometimes referred to as a receiver bias electrode. In the example shown in FIG. 9, at least a portion of the apparatus 200 includes an ultrasonic transmitter 927 that can function as a plane-wave ultrasonic transmitter. The ultrasonic transmitter 927 may, for example, include a piezoelectric transmitter layer with transmitter excitation electrodes disposed on each side of the piezoelectric transmitter layer.

Here, the incident light 911 causes optical excitation within the finger 806 and resultant acoustic wave generation. In this example, the generated acoustic waves 913 include ultrasonic waves. Acoustic emissions generated by the absorption of incident light may be detected by the ultrasonic receiver 202. A high signal-to-noise ratio may be obtained because the resulting ultrasonic waves are caused by optical stimulation instead of by reflection of transmitted ultrasonic waves.

In this example, the apparatus 200 includes a control system, although the control system is not shown in FIG. 9. According to some examples, the control system may be configured for discriminating between vein heart rate waveforms and artery heart rate waveforms by obtaining depth-discriminated signals. According to some such examples, receiving the signals from the piezoelectric receiver involves obtaining depth-discriminated signals by selecting an acquisition time window to receive acoustic waves emitted from a range of different depths within a target object, such as a finger, a wrist, an car, etc. In some examples, depth-discriminated signals may be obtained by a process of partitioning the acoustic waves received during the RGW into a plurality of smaller time windows, e.g., as described above. Each of the time windows may correspond to a depth range inside the target object from which the acoustic waves are received. According to some alternative examples, receiving the signals from the piezoelectric receiver involves obtaining depth-discriminated signals by applying first through $N^{th}$ acquisition time delays and receiving first through $N^{th}$ signals during first through $N^{th}$ acquisition time windows, each of the first through $N^{th}$ acquisition time windows occurring after a corresponding one of the first through $N^{th}$ acquisition time delays, wherein N is an integer greater than one. The control system may be configured for determining vein heart rate waveforms and artery heart rate waveforms based, at least in part, on the depth-discriminated signals.

Figure 10:
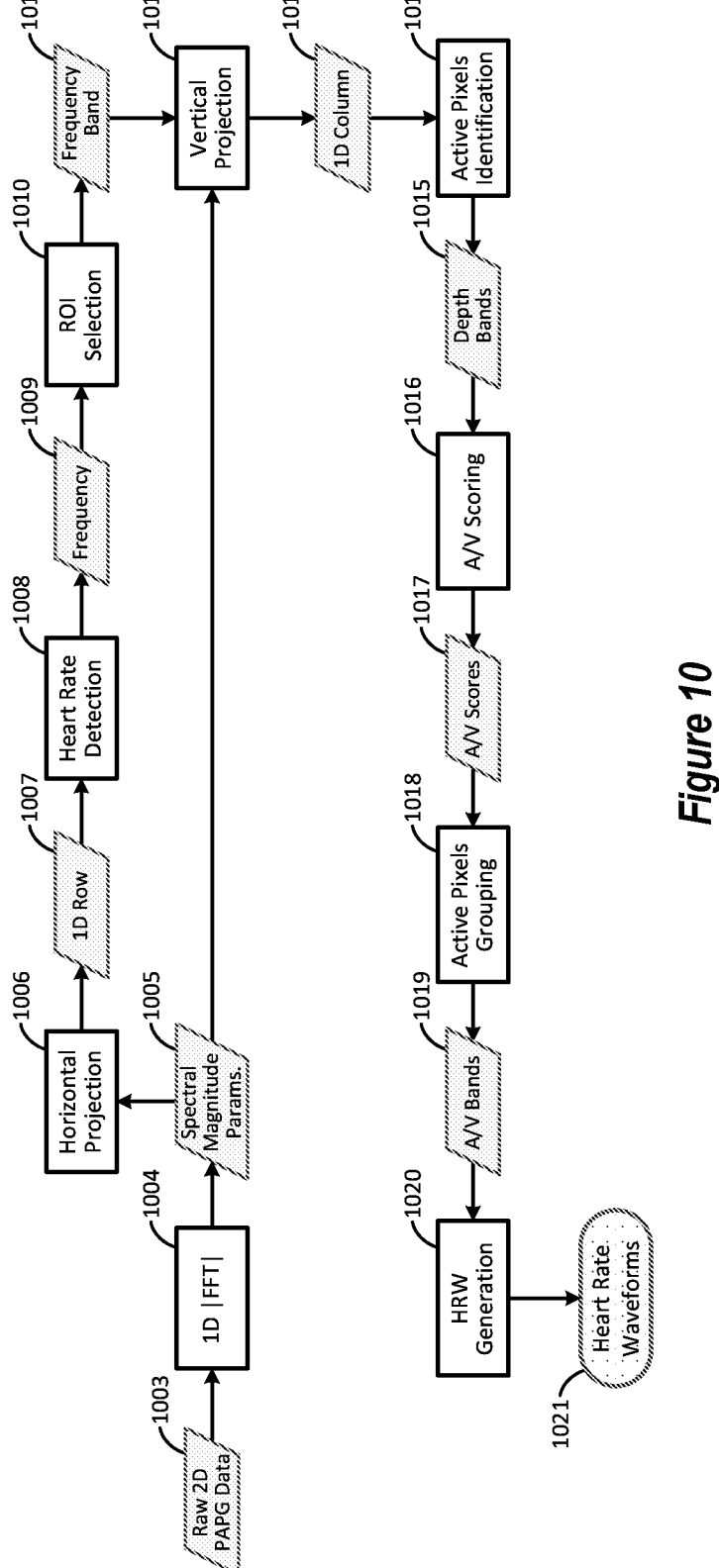
FIG. 10 is a block diagram that illustrates an example heart rate wave generation process according to some implementations.

FIG. 10 is a block diagram that illustrates an example heart rate wave generation process 1000 according to some implementations. According to heart rate wave generation process 1000, raw 2D PAPG data 1003 can be subjected to one-dimensional fast Fourier transformation at 1004 to obtain spectral magnitude parameters 1005 associated with raw 2D PAPG data 1003. Based on the spectral magnitude parameters 1005, horizontal projection can be conducted at 1006 to obtain a 1D row 1007. Heart rate detection can be performed at 1008 to identify a frequency 1009 based on the 1D row 1007. The frequency 1009 can serve as a basis for region-of-interest (ROI) selection at 1010, which can result in selection of a frequency band 1011. Based on the spectral magnitude parameters 1005 and the frequency band 1011, vertical projection can be conducted at 1012 to obtain a 1D column 1013. Active pixels identification can be performed at 1014 to determine depth bands 1015 based on 1D column 1013. Depth bands 1015 can serve as input to artery/vein (A/V) scoring at 1016, which can yield A/V scores 1017. Active pixels grouping at 1018 can determine A/V bands 1019 based on A/V scores 1017. Heart rate wave generation can be conducted at 1020 in accordance with the determination of A/V bands 1019, to produce heart rate waveforms 1021.

In some implementations, some or all of the components of apparatus 200 of FIG. 2 may be arranged, assembled or otherwise included within a single housing of a single ambulatory monitoring device. In some examples, the housing and other components of the ambulatory monitoring device can be configured such that when the ambulatory monitoring device is affixed or otherwise physically coupled to a subject, light source system 204 will emit light pulses into tissue along a stretch of an artery along which various arterial properties can be assumed to be relatively constant. In various implementations, the housing of the ambulatory monitoring device is a wearable housing or is incorporated into or integrated with a wearable housing. In some specific implementations, the wearable housing includes (or is connected with) a physical coupling mechanism for removable non-invasive attachment to the user. The housing can be formed using any of a variety of suitable manufacturing processes, including injection molding and vacuum forming, among others. In addition, the housing can be made from any of a variety of suitable materials, including, but not limited to, plastic, metal, glass, rubber and ceramic, or combinations of these or other materials. In various implementations, the housing and coupling mechanism can enable full ambulatory use. In other words, some implementations of the wearable monitoring devices described herein are noninvasive, not physically-inhibiting and generally do not restrict the free uninhibited motion of a subject's arms or legs, enabling continuous or periodic monitoring of cardiovascular characteristics such as blood pressure even as the subject is mobile or otherwise engaged in a physical activity. As such, the ambulatory monitoring device can facilitate and enable long-term wearing and monitoring (for example, over days, weeks or a month or more without interruption) of one or more biological characteristics of interest to obtain a better picture of such characteristics over extended durations of time, and generally, a better picture of the user's health.

Figure 11A:
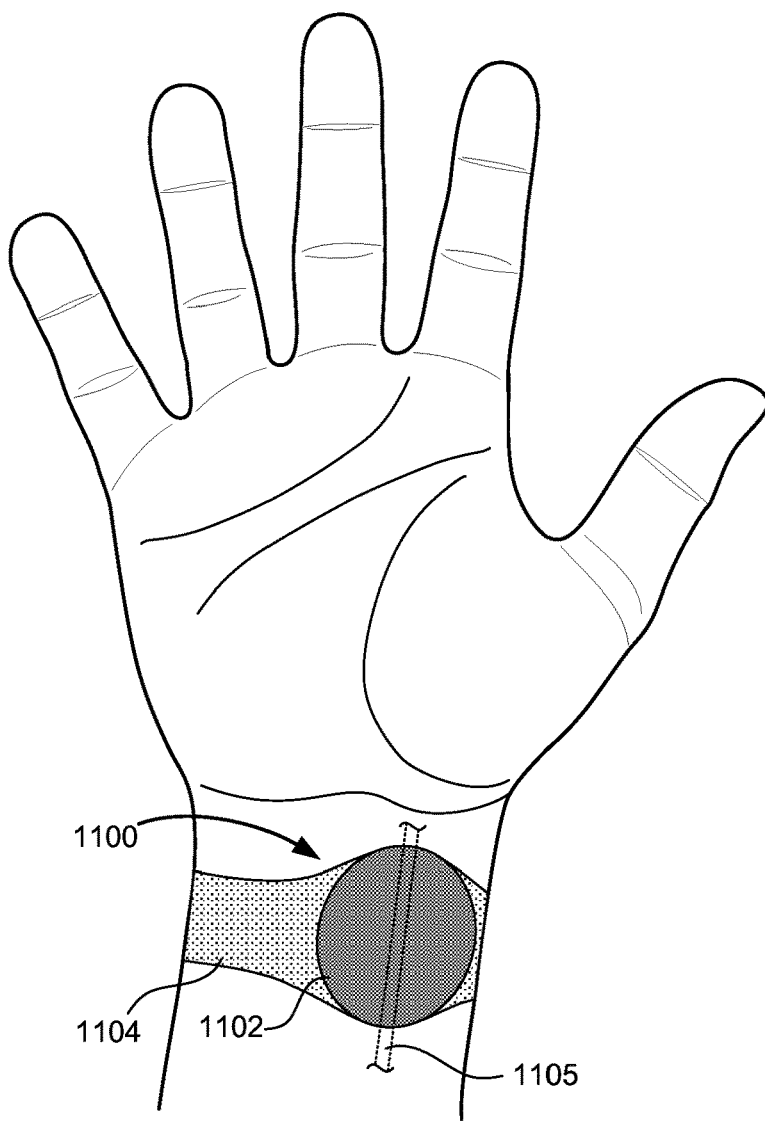
FIG. 11A shows an example ambulatory monitoring device 1100 designed to be worn around a wrist according to some implementations.

In some implementations, some or all of the components of apparatus 200 of FIG. 2 may be arranged, assembled or otherwise included within a housing of an ambulatory monitoring device that can be positioned around a wrist of a user with a strap or band, similar to a watch or fitness/ activity tracker. FIG. 11A shows an example ambulatory monitoring device 1100 designed to be worn around a wrist according to some implementations. In the illustrated example, the monitoring device 1100 includes a housing 1102 integrally formed with, coupled with or otherwise integrated with a strap or band 1104. In this example, the ambulatory monitoring device 1100 is coupled around the wrist such that a light source system within the housing 1102 will emit light pulses into tissue along a stretch of an artery 1105.

Figure 11B:
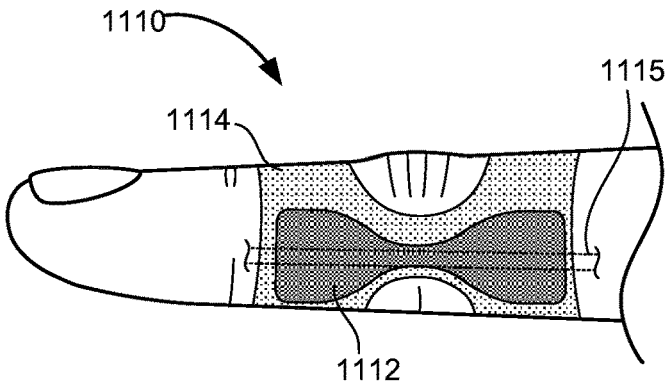
FIG. 11B shows an example ambulatory monitoring device 1110 designed to be worn around a finger according to some implementations.

In some other implementations, some or all of the components of apparatus 200 of FIG. 2 may be arranged, assembled or otherwise included within a housing of an ambulatory monitoring device that can similarly be designed or adapted for positioning around a forearm, an upper arm, an ankle, a lower leg, an upper leg, or a finger, using a strap or band. FIG. 11B shows an example ambulatory monitoring device 1110 designed to be worn around a finger according to some implementations. In the illustrated example, the monitoring device 1110 includes a housing 1112 integrally formed with, coupled with or otherwise integrated with a strap or band 1114. In this example, the ambulatory monitoring device 1110 is coupled around the finger such that a light source system within the housing 1112 will emit light pulses into tissue along a stretch of an artery 1115.

In yet other implementations, some or all of the components of apparatus 200 of FIG. 2 may be arranged, assembled or otherwise included within a housing of an ambulatory monitoring device that can be positioned on a region of interest of the user without the use of a strap or band. For example, some or all of the components of apparatus 200 of FIG. 2 may be arranged, assembled or otherwise included within a housing that is secured to the skin of a region of interest of the user using an adhesive or other suitable attachment mechanism (an example of a "patch" monitoring device).

Figure 11C:
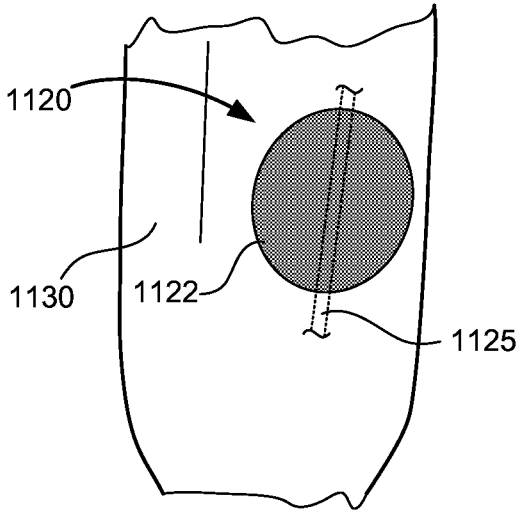
FIG. 11C shows an example ambulatory monitoring device 1120 designed to reside on an earbud according to some implementations.

FIG. 11C shows an example ambulatory monitoring device 1120 designed to reside on an earbud according to some implementations. According to this example, the ambulatory monitoring device 1120 is coupled to the housing of an earbud 1130. In this example, the ambulatory monitoring device 1120 is positioned such that a light source system within the housing 1122 will emit light pulses into tissue along a stretch of an artery 1125.

Implementation examples are described in the following numbered clauses:

Clause 1. A biometric system, including a heart rate waveform analyzer configured to monitor a heart rate waveform associated with a subject to detect cardiac cycle markers, and determine a cardiac phase transition window based on the cardiac cycle markers, a photoacoustic sampling system, including a piezoelectric receiver, and a light source system, and a control system configured to activate the photoacoustic sampling system at a start of the cardiac phase transition window, during the cardiac phase transition window control the light source system to emit a plurality of light pulses into biological tissue of the subject, the biological tissue including blood and blood vessels at depths within the biological tissue, receive, from the piezoelectric receiver, signals corresponding to acoustic waves emitted from portions of the biological tissue, the acoustic waves corresponding to photoacoustic emissions from the blood and the blood vessels caused by the plurality of light pulses, and obtain plethysmography data based on the signals, and deactivate the photoacoustic sampling system by an end of the cardiac phase transition window.

Clause 2. The biometric system of clause 1, where the control system is further configured to deactivate the photoacoustic sampling system prior to the end of the cardiac phase transition window responsive to a determination, prior to the end of the cardiac phase transition window, that the plethysmography data includes at least a threshold number of samples.

Clause 3. The biometric system of any of clauses 1 to 2, where the cardiac phase transition window corresponds to a systolic-to-diastolic transition.

Clause 4. The biometric system of any of clauses 1 to 2, where the cardiac phase transition window corresponds to a diastolic-to-systolic transition.

Clause 5. The biometric system of any of clauses 1 to 4, where the heart rate waveform analyzer is further configured to obtain the heart rate waveform based on a data stream received from a heart activity sensor.

Clause 6. The biometric system of any of clauses 1 to 5, where the control system is further configured to determine a blood pressure based on the plethysmography data, and display the blood pressure on a display.

Clause 7. The biometric system of clause 6, where the control system is further configured to determine the blood pressure based on systolic phase data included in the plethysmography data, without reference to diastolic phase data included in the plethysmography data.

Clause 8. The biometric system of any of clauses 1 to 7, where the plethysmography data is photoacoustic plethysmography (PAPG) data.

Clause 9. The biometric system of clause 8, where the control system is further configured to generate a two-dimensional (2D) PAPG image based on the PAPG data.

Clause 10. The biometric system of clause 9, where the 2D PAPG image includes a depth time dimension and a pulse time dimension.

Clause 11. A biometric method, including monitoring a heart rate waveform associated with a subject to detect cardiac cycle markers, determining a cardiac phase transition window based on the cardiac cycle markers, activating a photoacoustic sampling system at a start of the cardiac phase transition window, the photoacoustic sampling system including a piezoelectric receiver and a light source system, during the cardiac phase transition window controlling the light source system to emit a plurality of light pulses into biological tissue of the subject, the biological tissue including blood and blood vessels at depths within the biological tissue, receiving, from the piezoelectric receiver, signals corresponding to acoustic waves emitted from portions of the biological tissue, the acoustic waves corresponding to photoacoustic emissions from the blood and the blood vessels caused by the plurality of light pulses, and obtaining plethysmography data based on the signals, and deactivating the photoacoustic sampling system by an end of the cardiac phase transition window.

Clause 12. The biometric method of clause 11, further including deactivating the photoacoustic sampling system prior to the end of the cardiac phase transition window responsive to a determination, prior to the end of the cardiac phase transition window, that the plethysmography data includes at least a threshold number of samples.

Clause 13. The biometric method of any of clauses 11 to 12, where the cardiac phase transition window corresponds to a systolic-to-diastolic transition.

Clause 14. The biometric method of any of clauses 11 to 12, where the cardiac phase transition window corresponds to a diastolic-to-systolic transition.

Clause 15. The biometric method of any of clauses 11 to 14, further including obtaining the heart rate waveform based on a data stream received from a heart activity sensor.

Clause 16. The biometric method of any of clauses 11 to 15, further including determining a blood pressure based on the plethysmography data, and displaying the blood pressure on a display.

Clause 17. The biometric method of clause 16, further including determining the blood pressure based on systolic phase data included in the plethysmography data, without reference to diastolic phase data included in the plethysmography data.

Clause 18. The biometric method of any of clauses 11 to 17, where the plethysmography data is photoacoustic plethysmography (PAPG) data.

Clause 19. The biometric method of clause 18, further including generating a two-dimensional (2D) PAPG image based on the PAPG data.

Clause 20. The biometric method of clause 19, where the 2D PAPG image includes a depth time dimension and a pulse time dimension.

Clause 21. One or more non-transitory media having software stored thereon, the software including instructions for controlling one or more devices to perform a biometric method, the biometric method including monitoring a heart rate waveform associated with a subject to detect cardiac cycle markers, determining a cardiac phase transition window based on the cardiac cycle markers, activating a photoacoustic sampling system at a start of the cardiac phase transition window, the photoacoustic sampling system including a piezoelectric receiver and a light source system, during the cardiac phase transition window controlling the light source system to emit a plurality of light pulses into biological tissue of the subject, the biological tissue including blood and blood vessels at depths within the biological tissue, receiving, from the piezoelectric receiver, signals corresponding to acoustic waves emitted from portions of the biological tissue, the acoustic waves corresponding to photoacoustic emissions from the blood and the blood vessels caused by the plurality of light pulses, and obtaining plethysmography data based on the signals, and deactivating the photoacoustic sampling system by an end of the cardiac phase transition window.

Clause 22. The one or more non-transitory media of clause 21, where the biometric method further includes deactivating the photoacoustic sampling system prior to the end of the cardiac phase transition window responsive to a determination, prior to the end of the cardiac phase transition window, that the plethysmography data includes at least a threshold number of samples.

Clause 23. The one or more non-transitory media of any of clauses 21 to 22, where the cardiac phase transition window corresponds to a systolic-to-diastolic transition.

Clause 24. The one or more non-transitory media of any of clauses 21 to 22, where the cardiac phase transition window corresponds to a diastolic-to-systolic transition.

Clause 25. The one or more non-transitory media of any of clauses 21 to 24, where the biometric method further includes obtaining the heart rate waveform based on a data stream received from a heart activity sensor.

Clause 26. The one or more non-transitory media of any of clauses 21 to 25, where the biometric method further includes determining a blood pressure based on the plethysmography data, and displaying the blood pressure on a display.

Clause 27. The one or more non-transitory media of clause 26, where the biometric method further includes determining the blood pressure based on systolic phase data included in the plethysmography data, without reference to diastolic phase data included in the plethysmography data.

Clause 28. The one or more non-transitory media of any of clauses 21 to 27, where the plethysmography data is photoacoustic plethysmography (PAPG) data.

Clause 29. The one or more non-transitory media of clause 28, where the biometric method further includes generating a two-dimensional (2D) PAPG image based on the PAPG data.

Clause 30. The one or more non-transitory media of clause 29, where the 2D PAPG image includes a depth time dimension and a pulse time dimension.

Clause 31. An apparatus including a photoacoustic system, including a piezoelectric receiver, and a light source system, and a control system configured to receive heart rate waveform data from a heart rate waveform analyzer, activate the photoacoustic sampling system at a start of a cardiac phase transition window indicated by the heart rate waveform data, during the cardiac phase transition window control the light source system to emit a plurality of light pulses into biological tissue of a subject, the biological tissue including blood and blood vessels at depths within the biological tissue, receive, from the piezoelectric receiver, signals corresponding to acoustic waves emitted from portions of the biological tissue, the acoustic waves corresponding to photoacoustic emissions from the blood and the blood vessels caused by the plurality of light pulses, and obtain plethysmography data based on the signals, and deactivate the photoacoustic sampling system by an end of the cardiac phase transition window.

Clause 32. The apparatus of clause 31, where the control system is further configured to deactivate the photoacoustic sampling system prior to the end of the cardiac phase transition window responsive to a determination, prior to the end of the cardiac phase transition window, that the plethysmography data includes at least a threshold number of samples.

Clause 33. The biometric system of any of clauses 31 to 32, where the cardiac phase transition window corresponds to a systolic-to-diastolic transition.

Clause 34. The biometric system of any of clauses 31 to 32, where the cardiac phase transition window corresponds to a diastolic-to-systolic transition.

Clause 35. The biometric system of any of clauses 31 to 34, where the heart rate waveform analyzer is configured to obtain the heart rate waveform based on a data stream received from a heart activity sensor.

Clause 36. The biometric system of any of clauses 31 to 35, where the control system is further configured to determine a blood pressure based on the plethysmography data, and display the blood pressure on a display.

Clause 37. The biometric system of clause 36, where the control system is further configured to determine the blood pressure based on systolic phase data included in the plethysmography data, without reference to diastolic phase data included in the plethysmography data.

Clause 38. The biometric system of any of clauses 31 to 37, where the plethysmography data is photoacoustic plethysmography (PAPG) data.

Clause 39. The biometric system of clause 38, where the control system is further configured to generate a two-dimensional (2D) PAPG image based on the PAPG data.

Clause 40. The biometric system of clause 39, where the 2D PAPG image includes a depth time dimension and a pulse time dimension.

The terms "estimating," "measuring," "calculating," "inferring," "deducing," "evaluating," "determining" and "monitoring" may be used interchangeably herein where appropriate unless otherwise indicated. Similarly, derivations from the roots of these terms also are used interchangeably where appropriate; for example, the terms "estimate," "measurement," "calculation," "inference" and "determination" also are used interchangeably herein.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

Various modifications to the implementations described in this disclosure may be readily apparent to those skilled in the art, and the generic principles defined herein may be applied to other implementations without departing from the spirit or scope of this disclosure. Thus, the following claims are not intended to be limited to the implementations shown herein, but are to be accorded the widest scope consistent with this disclosure, the principles and the novel features disclosed herein.

Additionally, certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. Moreover, various ones of the described and illustrated operations can itself include and collectively refer to a number of sub-operations. For example, each of the operations described above can itself involve the execution of a process or algorithm. Furthermore, various ones of the described and illustrated operations can be combined or performed in parallel in some implementations. Similarly, the separation of various system components in the implementations described above should not be understood as requiring such separation in all implementations. As such, other implementations are within the scope of the following claims. In some cases, the actions recited in the claims can be performed in a different order and still achieve desirable results.

The invention claimed is:

1. A biometric system, comprising:
a heart rate waveform analyzer configured to:
  monitor a heart rate waveform associated with a subject to detect cardiac cycle markers; and
  determine one or more cardiac phase transition windows based on the cardiac cycle markers;
a photoacoustic sampling system, including:
  a piezoelectric receiver; and
  a light source system; and
a control system configured to:
  activate the photoacoustic sampling system at a start of a first cardiac phase transition window of the one or more cardiac phase transition windows, the first cardiac phase transition window corresponding to a systolic-to-diastolic transition;
  during the first cardiac phase transition window:
    control the light source system to emit a first plurality of light pulses into biological tissue of the subject, the biological tissue including blood and blood vessels at depths within the biological tissue;

receive, from the piezoelectric receiver, first signals corresponding to acoustic waves emitted from the biological tissue and corresponding to photoacoustic emissions from the blood and the blood vessels caused by the first plurality of light pulses; and obtain first plethysmography data based on the first signals; and deactivate the photoacoustic sampling system by an end of the first cardiac phase transition window, wherein the control system is further configured to:

activate the photoacoustic sampling system at a start of a second cardiac phase transition window of the one or more cardiac phase transition windows, the second cardiac phase transition window corresponding to a diastolic-to-systolic transition;

during the second cardiac phase transition window:

control the light source system to emit a second plurality of light pulses into the biological tissue of the subject;

receive, from the piezoelectric receiver, second signals corresponding to acoustic waves emitted from the biological tissue and corresponding to photoacoustic emissions from the blood and the blood vessels caused by the second plurality of light pulses; and obtain second plethysmography data based on the second signals; and deactivate the photoacoustic sampling system by an end of the second cardiac phase transition window; wherein the heart rate waveform analyzer and the control system include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

2. The biometric system of claim 1, wherein the control system is further configured to deactivate the photoacoustic sampling system prior to the end of the first cardiac phase transition window responsive to a determination that the first plethysmography data includes at least a threshold number of samples.

3. The biometric system of claim 1, wherein the heart rate waveform analyzer is further configured to obtain the heart rate waveform based on a data stream received from a heart activity sensor.

4. The biometric system of claim 1, wherein the control system is further configured to: determine a blood pressure based on the first plethysmography data and the second plethysmography data; and display the blood pressure on a display.

5. The biometric system of claim 4, wherein the control system is further configured to determine the blood pressure based on systolic phase data comprised in the first plethysmography data, without reference to diastolic phase data comprised in the second plethysmography data.

6. The biometric system of claim 1, wherein the first plethysmography data and the second plethysmography data are photoacoustic plethysmography (PAPG) data.

7. The biometric system of claim 6, wherein the control system is further configured to generate a two-dimensional (2D) PAPG image based on the PAPG data.

8. The biometric system of claim 7, wherein the 2D PAPG image comprises a depth time dimension and a pulse time dimension.

32

9. A biometric method, comprising:

monitoring a heart rate waveform associated with a subject to detect cardiac cycle markers;

determining one or more cardiac phase transition windows based on the cardiac cycle markers;

activating a photoacoustic sampling system at a start of a first cardiac phase transition window of the one or more cardiac phase transition windows, the first cardiac phase transition window corresponding to a systolic-to-diastolic transition, the photoacoustic sampling system including a piezoelectric receiver and a light source system;

during the first cardiac phase transition window:

controlling the light source system to emit a first plurality of light pulses into biological tissue of the subject, the biological tissue including blood and blood vessels at depths within the biological tissue;

receiving, from the piezoelectric receiver, first signals corresponding to acoustic waves emitted from the biological tissue and corresponding to photoacoustic emissions from the blood and the blood vessels caused by the first plurality of light pulses; and obtaining first plethysmography data based on the first signals; and deactivating the photoacoustic sampling system by an end of the first cardiac phase transition window;

activating the photoacoustic sampling system at a start of a second cardiac phase transition window of the one or more cardiac phase transition windows, the second cardiac phase transition window corresponding to a diastolic-to-systolic transition;

during the second cardiac phase transition window:

controlling the light source system to emit a second plurality of light pulses into biological tissue of the subject;

receiving, from the piezoelectric receiver, second signals corresponding to acoustic waves emitted from the biological tissue and corresponding to photoacoustic emissions from the blood and the blood vessels caused by the second plurality of light pulses; and obtaining second plethysmography data based on the second signals; and deactivating the photoacoustic sampling system by an end of the second cardiac phase transition window.

10. The biometric method of claim 9, further comprising deactivating the photoacoustic sampling system prior to the end of the first cardiac phase transition window responsive to a determination, that the first plethysmography data includes at least a threshold number of samples.

11. The biometric method of claim 9, further comprising obtaining the heart rate waveform based on a data stream received from a heart activity sensor.

12. The biometric method of claim 9, further comprising: determining a blood pressure based on the first plethysmography data and the second plethysmography data; and displaying the blood pressure on a display.

13. The biometric method of claim 12, further comprising determining the blood pressure based on systolic phase data comprised in the first plethysmography data, without reference to diastolic phase data comprised in the second plethysmography data.

14. The biometric method of claim 9, wherein the first plethysmography data and the second plethysmography data are photoacoustic plethysmography (PAPG) data.

15. The biometric method of claim 14, further comprising generating a two-dimensional (2D) PAPG image based on the PAPG data.

16. The biometric method of claim 15, wherein the 2D PAPG image comprises a depth time dimension and a pulse time dimension.

17. One or more non-transitory media having software stored thereon, the software including instructions for controlling one or more devices to perform a biometric method, the biometric method comprising:

monitoring a heart rate waveform associated with a subject to detect cardiac cycle markers;

determining one or more cardiac phase transition windows based on the cardiac cycle markers;

activating a photoacoustic sampling system at a start of a first cardiac phase transition window of the one or more cardiac phase transition windows, the first cardiac phase transition window corresponding to a systolic-to-diastolic transition, the photoacoustic sampling system including a piezoelectric receiver and a light source system;

during the first cardiac phase transition window:

controlling the light source system to emit a first plurality of light pulses into biological tissue of the subject, the biological tissue including blood and blood vessels at depths within the biological tissue;

receiving, from the piezoelectric receiver, first signals corresponding to acoustic waves emitted from the biological tissue and corresponding to photoacoustic emissions from the blood and the blood vessels caused by the first plurality of light pulses; and obtaining first plethysmography data based on the first signals; and deactivating the photoacoustic sampling system by an end of the first cardiac phase transition window;

activating the photoacoustic sampling system at a start of a second cardiac phase transition window of the one or more cardiac phase transition windows, the second cardiac phase transition window corresponding to a diastolic-to-systolic transition;

during the second cardiac phase transition window:

controlling the light source system to emit a second plurality of light pulses into biological tissue of the subject;

receiving, from the piezoelectric receiver, second signals corresponding to acoustic waves emitted from the biological tissue and corresponding to photoacoustic emissions from the blood and the blood vessels caused by the second plurality of light pulses; and obtaining second plethysmography data based on the second signals; and deactivating the photoacoustic sampling system by an end of the second cardiac phase transition window.

18. The one or more non-transitory media of claim 17, wherein the biometric method further comprises deactivating the photoacoustic sampling system prior to the end of the first cardiac phase transition window responsive to a determination that the first plethysmography data includes at least a threshold number of samples.

19. The one or more non-transitory media of claim 17, wherein the biometric method further comprises obtaining the heart rate waveform based on a data stream received from a heart activity sensor.

20. The one or more non-transitory media of claim 17, wherein the biometric method further comprises: determining a blood pressure based on the first plethysmography data and the second plethysmography data; and displaying the blood pressure on a display.

21. The one or more non-transitory media of claim 20, wherein the biometric method further comprises determining the blood pressure based on systolic phase data comprised in the first plethysmography data, without reference to diastolic phase data comprised in the second plethysmography data.

22. The one or more non-transitory media of claim 17, wherein the first plethysmography data and the second plethysmography data are photoacoustic plethysmography (PAPG) data.

23. An apparatus comprising:

a photoacoustic system, including:

a piezoelectric receiver; and a light source system; and a control system configured to:

receive heart rate waveform data, the heart rate waveform data indicating one or more cardiac phase transition windows based on cardiac cycle markers, from a heart rate waveform analyzer;

activate the photoacoustic sampling system at a start of a first cardiac phase transition window indicated by the heart rate waveform data, the first cardiac phase transition window corresponding to a systolic-to-diastolic transition;

during the first cardiac phase transition window:

control the light source system to emit a first plurality of light pulses into biological tissue of a subject, the biological tissue including blood and blood vessels at depths within the biological tissue;

receive, from the piezoelectric receiver, first signals corresponding to acoustic waves emitted from the biological tissue and corresponding to photoacoustic emissions from the blood and the blood vessels caused by the first plurality of light pulses; and obtain first plethysmography data based on the first signals; and deactivate the photoacoustic sampling system by an end of the first cardiac phase transition window;

wherein the control system is further configured to:

activate the photoacoustic sampling system at a start of a second cardiac phase transition window of the one or more cardiac phase transition windows, the second cardiac phase transition window corresponding to a diastolic-to-systolic transition;

during the second cardiac phase transition window:

control the light source system to emit a second plurality of light pulses into the biological tissue of the subject;

receive, from the piezoelectric receiver, second signals corresponding to acoustic waves emitted from the biological tissue and corresponding to photoacoustic emissions from the blood and the blood vessels caused by the second plurality of light pulses; and obtain second plethysmography data based on the second signals; and deactivate the photoacoustic sampling system by an end of the second cardiac phase transition window.

24. The apparatus of claim 23, wherein the control system is further configured to deactivate the photoacoustic sampling system prior to the end of the first cardiac phase transition window responsive to a determination that the first plethysmography data includes at least a threshold number of samples.

* * * * *